(12) United States Patent
Raines et al.

(10) Patent No.: US 7,317,129 B2
(45) Date of Patent: Jan. 8, 2008

(54) CHEMICAL SYNTHESIS OF REAGENTS FOR PEPTIDE COUPLING

(75) Inventors: Ronald T. Raines, Madison, WI (US); Laura L. Kiessling, Madison, WI (US); Bradley L. Nilsson, Madison, WI (US); Yi He, Madison, WI (US); Matthew B. Soellner, Madison, WI (US); Ronald J. Hinklin, Longmont, CO (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/229,926

(22) Filed: Sep. 19, 2005

(65) Prior Publication Data

US 2006/0025578 A1 Feb. 2, 2006

Related U.S. Application Data

(62) Division of application No. 10/456,988, filed on Jun. 6, 2003, now Pat. No. 6,974,884.

(60) Provisional application No. 60/387,171, filed on Jun. 7, 2002.

(51) Int. Cl.
C07F 5/02 (2006.01)
(52) U.S. Cl. .................... 568/2; 564/123; 530/402
(58) Field of Classification Search .............. 568/2; 530/402
See application file for complete search history.

(56) References Cited

U.S. PATENT DOCUMENTS

| 5,300,278 | A | 4/1994 | Pasqualini et al. |
| 5,541,289 | A | 7/1996 | Gilbertson |
| 5,543,389 | A | 8/1996 | Yatvin et al. |
| 6,974,884 | B2 * | 12/2005 | Raines et al. .................. 568/2 |
| 2002/0016003 | A1 | 2/2002 | Saxon et al. |
| 2003/0199084 | A1 | 10/2003 | Saxon et al. |

FOREIGN PATENT DOCUMENTS

| WO | 0168565 | 9/2001 |
| WO | 0187920 | 11/2001 |
| WO | 0218417 | 3/2002 |
| WO | 03104243 | 12/2003 |

OTHER PUBLICATIONS

Alfonso, C.A. (1998), "Studies on the Transformation of Azido-Group to N-(t-Butoxycarbonyl)amino Group via Staudinger Reaction," Synthetic Commun. 28:261-276.
Ariza et al. (1998), "One-Pot Conversion of Azides to Boc-Protected Amines with Trimethylphosphine and Boc-ON," Tetrahedron Lett. 39:9101-9102.
Ariza et al. (Jul. 2001), "From Vacinal Azido Alcohols to Boc-Amino Alcohols or Oxazolidinones, with Trimethylphosphine and Boc2O or CO2," Tetrahedron Lett. 42:4995-4999.
Ayers et al. (Feb. 1999), "Introduction of Unnatural Amino Acids into Proteins Using Expressed Protein Ligation," Biopolymers, 51:343-354.
Backes et al. (Mar. 1999), "An Alkanesulfonamide 'Safety-Catch' Linker for Solid-Phase Synthesis," J. Org. Chem. 64:2322-2330.
Block et al. (1989), "2-Phosphino- and 2-Phosphinylbenzenethiols: New Ligand Types," J. Am. Chem. Soc. 111: 2327-2329.
Borgia et al. (Jun. 2000), "Chemical Synthesis of Proteins," Trends Biotechnol. 18:243-251.
Bosch et al. (1993) "Alternative Procedures for Macrolactamisation of Omega-Azido Acids," Tetrahedron Lett. 34:4671-4674.
Bosch et al. (1995), "Epimerisation-free Peptide Formation from Carboxylic Acid Anhydrides and Azido Derivatives," J. Chem. Soc., Chem. Commun., pp. 91-92.
Bosch et al. (1996), "On the Reaction of Acyl Chlorides and Carboxylic Anhydrides with Phosphazene," J. Org. Chem. 61:5638-5643.
Boullanger et al. (Feb. 2000), "Syntheses of Amphiphilic Glycosylamides from Glycosyl Azides Without Transient Reduction to Glycosylamines," Carbohydr. Res. 324:97-106.
Brik et al. (Jun. 2000), "Protein Synthesis by Solid-Phase Chemical Ligation Using a Safety Catch Linker," J. Org. Chem. 65(12):3829-3835.
Brisset et al. (1993), "Phosphine-Borane Complexes; Direct Use in Asymmetric Catalysis," Tetrahedron Lett. 34:4523-4526.
Bruice et al. (1960), "The Effect of Geminal Substitution Ring Size and Rotamer Distribution on the Intramolecular Nucleophilic Catalysis of the Hydrolysis of Monophenyl Esters of Dibasic Acids and the Solvolysis of the Intermediate Anhydrides," J. Am. Chem. Soc. 82:5858-5865.
Brunel et al. (1998), "Phosphane-Boranes: Synthesis, Characterization and Synthetic Applications," Coord. Chem. Rev. 180:665-698.
Cane et al. (1998), "Harnessing the Biosynthetic Code: Combinations, Permutations, and Mutations," Science 282:63-68.
Carboni et al. (Jan. 1999), "Recent Developments in the Chemistry of Amine- and Phosphine-Boranes," Tetrahedron 55:1197-1248.
Charrier et al. (1978), "La Diphenyl-Cyclopentadienylmethyl-Phosphine FT SFS Complexes," (in French) Tetrahedron Lett. 27:2407-2410.
Cotton et al. (Sep. 1999), "Peptide Ligation and its Application to Protein Engineering," Chem. Biol. 6: R247-R256.
Dawson et al. (Jul. 2000), "Synthesis of Native Proteins by Chemical Ligation," Annu. Rev. Biochem. 69:923-960.

(Continued)

Primary Examiner—Samuel A Barts
(74) Attorney, Agent, or Firm—Greenlee, Winner and Sullivan, P.C.

(57) ABSTRACT

The present invention provides improved methods for synthesis of phosphinothiol reagents, as well as novel protected reagents, for use in formation of amide bonds, and particularly, for peptide ligation. The invention provides phosphine-borane complexes useful as reagents in the formation of amide bonds, particularly for the formation of an amide bond between any two of an amino acid, a peptide, or a protein.

28 Claims, No Drawings

OTHER PUBLICATIONS

Dawson et al. (1994), "Synthesis of Proteins by Native Chemical Ligation," Science 266:776-779.

Dawson et al. (1997), "Modulation of Reactivity in Native Chemical Ligation through the Use of Thiol Additives," J. Am. Chem. Soc. 119:4325-4329.

Drijfhout et al. (Dec. 2000), Chemical Abstracts (Columbus, Ohio, USA) No. 133:135556. Abstract of "Methods of Preparing Peptide-Carrier Conjugates," in Fmoc Solid Phase Peptide Synthesis), pp. 229-241.

Evans et al. (1998), "Semisynthesis of Cytotoxic Proteins Using a Modified Protein Splicing Element," Protein Sci. 7:2256-2264.

Evans et al. (pub. on-line Feb. 2000), "Intein-Mediated Protein Ligation: Harnessing Nature's Escape Artists," Biopolymers 51:333-342.

Farrington et al. (1989), "A Convenient Synthesis of Diethyl (Mercaptomethyl)Phosphonate," Org. Prep. Proced. Int. 21:390-392.

Friedman, M. (Apr. 1999), "Lysinoalanine in Food and in Antimicrobial Proteins," Adv. Exp. Med. Biol. 459:145-159.

Garcia et al. (1984), "New Synthetic "Tricks". Triphenylphosphine-Mediated Amide Formation from Carboxylic Acids and Azides," Tetrahedron Lett. 25:4841-4844.

Garcia et al.(1986), "New Synthetic "Tricks". One-Pot Preparation of N-substituted Phthalimides from Azides and Phthalic Anhydride," Tetrahedron Lett. 27:639-640.

Gilbertson, S. (Aug. 2001), "High-Yielding Staudinger Ligation of Phosphinoesters and Azides to Form Amides," Chemtracts-Org. Chem. 14:524-528.

Gololobov et al. (1992), "Recent Advances in the Staudinger Reaction," Tetrahedron 48:1353-1406.

Gololobov et al. (1981), "Sixty Years of Staudinger Reaction," Tetrahedron 37: 437-472.

Holford et al. (1998), "Adding 'Splice' to Protein Engineering," Structure 15: 951-956.

Imamoto et al. (1990), "Synthesis and Reactions of Phosphine-Boranes. Synthesis of New Bidentate Ligands with Homochiral Phosphine Centers via Optically Pure Phosphine-Boranes," J. Am. Chem. Soc. 112:5244-5252.

Inazu et al. (1993), "A New Simple Method for the Synthesis of Nα-Fmoc-Nβ-Glycosylated-L-Asparagine Derivatives," Synlett., pp. 869-870.

Ingenito et al. ( Nov. 1999), "Solid Phase Synthesis of Peptide C-Terminal Thioesters by Fmoc/t-Bu Chemistry," J. Am. Chem. Soc. 121:11369-11374.

Janssen, M. J. The Chemistry of Carboxylic Acids and Esters: Patai, S., Ed.; Interscience Publishers: New York, 1969; pp. 730-736.

Jung et al. (1991), "Gem-Dialkyl Effect in the Intramolecular Diels-Alder Reaction of 2-Furfuryl Methyl Fumarates: The Reactive Rotamer Effect, Enthalpic Basis for Acceleration, and Evidence for a Polar Transition State," J. Am. Chem. Soc. 113: 224-232.

Kaiser, E. T. (1989), "Synthetic Approaches to Biologically Active Peptides and Proteins Including Enzymes," Acc. Chem. Res. 22:47-54.

Katz, L. (1997), "Manipulation of Modular Polyketide Syntheses," Chem. Rev. 97:2557-2575.

Keating et al. (Oct. 1999), "Initiation, Elongation, and Termination Strategies in Polyketide and Polypeptide Antibiotic Biosynthesis," Curr. Opin.Chem. Biol. 3:598-606.

Kemp et al. (1986), "Peptide Synthesis by Prior Thiol Capture. 1. A Convenient Synthesis of 4-Hydroxy-6-mercaptodibenzofuran and Novel Solid-Phase Synthesis of Peptide-Derived 4-(Acyloxy)-6-mercaptodibenzofurans," J. Org. Chem. 51:1821-1829.

Kent, S. B. (1988), "Chemical Synthesis of Peptides and Proteins," Annu. Rev. Biochem. 57: 957-989.

Khosla, C. (1997), "Harnessing the Biosynthetic Potential of Modular Polyketide Synthases," Chem. Rev. 97:2577-2590.

Kiick et al. (Jan. 2002), "Incorporation of Azides into Recombinant Proteins for Chemoselective Modification by the Slaudinger Ligation," Proc. Natl. Acad. Sci. USA 99:19-24.

Kochendoerfer et al. (Dec. 1999), "Chemical Protein Synthesis," Curr. Opin. Chem. Biol. 3:665-671.

Konz et al. (Feb. 1999), "How do Peptide Synthetases Generate Structural Diversity?" Chem. Biol. 6: R39-R48.

Lamoureux et al. (1993), "Synthesis of Dithiols as Reducing Agents for Disulfides in Neutral Aqueous Solution and Comparison of Reduction Potentials," J. Org. Chem. 58:633-641.

Leffler et al. (1967) "The Staudinger Reaction Between Triarylphosphines and Azides. A Study of the Mechanism," J. Am. Chem. Soc. 89:5235-5246.

He Y. et al. (2004) Organic. Lett. vol. 6:4479-4482.

* cited by examiner

CHEMICAL SYNTHESIS OF REAGENTS FOR PEPTIDE COUPLING

CROSS-REFERENCE TO RELATED APPLICATIONS

This application is a division of U.S. patent application Ser. No. 10/456,988, filed Jun. 6, 2003, now U.S. pat. 6,974,884, which takes priority under 35 U.S.C. 119(e) from U.S. provisional application Ser. No. 60/387,171, filed Jun. 7, 2002, both of which are incorporated by reference herein to the extent that it is not inconsistent with the disclosure herein.

STATEMENT REGARDING FEDERALLY SPONSORED RESEARCH OR DEVELOPMENT

This invention was made with U.S. Government support under National Institutes of Health Grant No. GM44783. The Government has certain rights in this invention.

BACKGROUND

The chemoselective ligation of peptides can be used to effect the total chemical synthesis of proteins.[1] The most common ligation method, native chemical ligation, relies on the presence of a cysteine residue at the N-terminus of each ligation junction.[2,3] Recently, we have reported[4] a peptide ligation method, a "Staudinger Ligation," that is universal, i.e., independent of the presence of any particular side chain This method is based on the Staudinger reaction, wherein a phosphine reduces an azide via a stable iminophosphorane intermediate.[5] Acylation of this iminophosphorane yields an amide.[6,7]

Scheme 1 illustrates our Staudinger Ligation which is further described in PCT application PCT/01/15440, filed May 11, 2000. A peptide fragment having a C-terminal phosphinothioester (2) reacts with another peptide fragment having an N-terminal azide (3). The resulting iminophosphorane (4) leads, after an S- to N-acyl shift, to an amidophosphonium salt (5). The P—N bond of the amidophosphonium salt is hydrolyzed readily to produce the amide product (6) and a phosphine oxide (7). Importantly, no residual atoms remain in the amide product.[4,6b], so the ligation is traceless. The phosphinothioester (2) is prepared by reaction of a of phosphinothiol reagent (1), such as $Ph_2CH_2$—SH, where Ph is a phenyl group. The Staudinger Ligation can generally be employed to form peptide bonds and as such can be employed to ligate two amino acids, a peptide or a protein with an amino acid or peptide or two proteins. More generally, the Staudinger Ligation can be employed to form amide bonds. The amide bond is formed between a thioester and an azide. In general, the reaction functions for any thioester and any azide. The thioester is converted into a phosphinothioester which then reacts with the azide. For example, the thioester group may be formed, at the carboxy group of an amino acid or at the carboxy terminus of a peptide or protein or at an acid side group of an amino acid or one or more amino acids in a peptide or protein. The azido group may be formed, for example, at the amino group of an amino acid or at the amino terminus of a peptide or protein or at a basic side group of an amino acid or one or more amino acids in a peptide or protein. The Staudinger Ligation may also be employed to ligate an amino acid, peptide or protein group to a carbohydrate group, which may be a mono-, di-, tri- or polysaccharide, or to a nucleoside. The Staudinger Ligation may also be employed to ligate an amino acid, a peptide or protein group to a reporter group, tag or label (e.g., a group whose presence can be detected by optical or mass spectrometry or other instrumental method), including a fluorescent or phosphorescent group, an isotopic label or a radiolabel.

All natural α-amino acids except glycine have a stereogenic center at their α-carbon.[8] To be an effective tool for the total chemical synthesis of proteins, a peptide ligation reaction must proceed without epimerization. The coupling of thioesters in native chemical ligation, which like the Staudinger Ligation (Scheme 1) involves transthioesterification followed by an S- to N-acyl shift,[2,3] is known to proceed without detectable racemization.[9] We have demonstrated that the Staudinger Ligation (Scheme 1) proceeds in near quantitative yield without detectable epimerization.

The Staudinger Ligation of Scheme 1 employs a phosphinothiol reagent (1). Previously reported methods of synthesis of such reagents[4a, 4b] generally proceed in low yield. Synthesis of the phosphinothiol of formula 1 where R and R' are phenyl groups requires four synthetic steps, two of which are problematic, with an overall yield of about 39%. Difficulties can also be encountered in the synthesis of reagents of formula 1 where R and R' are small alkyl groups, such as ethyl groups, due to instability of the reagent itself. Use of the Staudinger Ligation for the formation of amide bonds between a variety of species would be facilitated by the development of improved methods for the synthesis of phosphinothiol reagents and the development of such reagents with increased stability. This invention provides improvements for carrying out the Staudinger Ligation.

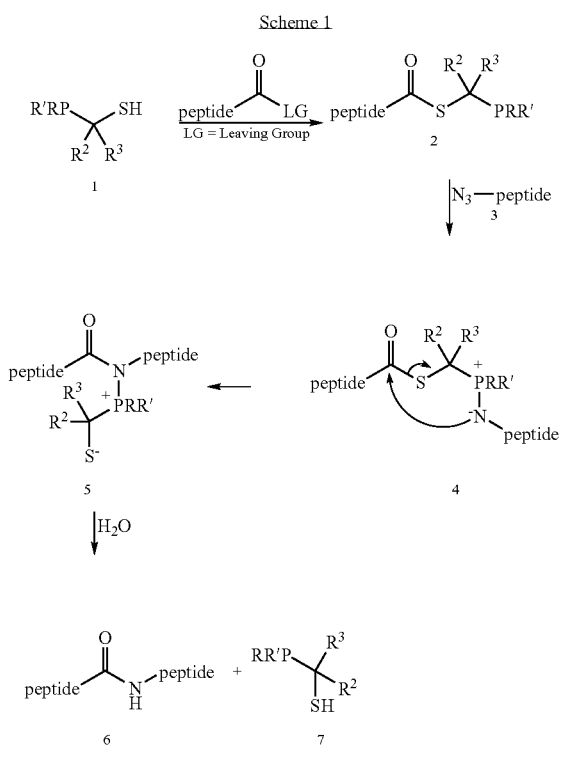

Scheme 1

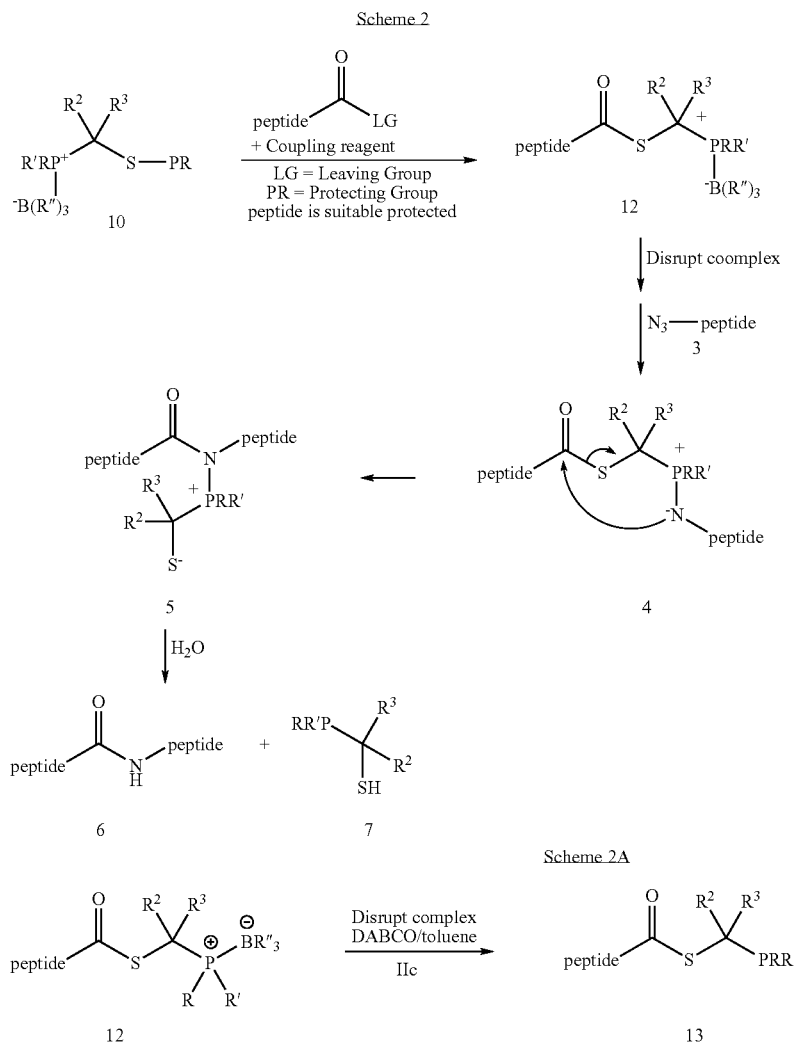

SUMMARY OF THE INVENTION

The present invention provides improved methods for synthesis of phosphinothiol reagents, as well as novel protected reagents, for use in formation of amide bonds, and particularly for peptide ligation as exemplified in Scheme 1 and Scheme 2.

In a specific embodiment, the invention provides improved methods for synthesis of phosphinothiols, e.g., 1 (Scheme 1), which were the most effective known phosphinothiols for effecting the Staudinger Ligation of peptides. In one aspect, the invention provides a synthesis of phosphinothiols themselves. In another aspect, the invention provides a protected phosphinothiol reagent (10, Scheme 2) which are phosphine-borane complexes which can be employed in the Staudinger Ligation to prepare phosphinothioesters.

A phosphinothiol reagent of this invention (1) is synthesized as illustrated in generalized Scheme 3 by reacting a protected alkylating agent of formula (20) where PR is a protecting group, particularly an acyl group —COR⁵ (defined below) and X is a leaving group (LG) with a phosphine-borane complex of formula (25, where R, R' and R" are defined as in formula 10, below) on deprotonation of the phosphine-borane complex to generate the protected phosphine-borane addition complex (10). The phosphinothiol reagent (1) is generated by disruption of the phosphine-borane complex (10) and removal of the protecting group (PR).

In specific embodiments, the protecting group PR is a —CO—R⁵ where R⁵ is H, an alkyl group, an aryl group or a substituted alkyl or a substituted aryl group. In specific embodiments, R and R' are aryl groups, particularly phenyl groups. In specific embodiments, R² and R³ are H or alkyl groups. In specific embodiments, R" are all hydrogen or are all small alkyl groups. In specific embodiments, X is a "good leaving group" as that term is understood in the art and specifically X can be a halogen, or a OTs, Otf, or OMs group.

Alternatively, the phosphine-borane complex of formula 10 can be used

The invention also provides phosphine-borane complexes of formula:

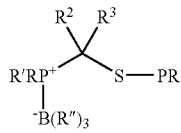

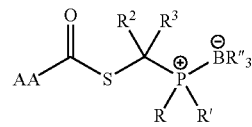

where:

PR is a suitable protecting group, which can include, among others, —CO—$R^5$ groups where $R^5$ can be selected from H, alkyl or aryl groups or substituted alkyl or aryl groups, where the substituents do not affect the function of PR as a protecting group for reactions illustrated herein;

R and R', independently of one another, are alkyl or aryl groups or substituted alkyl or aryl groups where the substituents do not significantly detrimentally affect the reactions as illustrated herein, R and R' may be the same or different groups, R and R' may be covalently linked to each other;

R", independently of other R" in the compound, can be H, an alkyl or aryl group or a substituted alkyl or aryl group where the substituents do not significantly negatively affect the formation of the phosphine-borane complex or significantly negatively affect the properties of B(R")$_3$ as a protective groups for the phosphine; all three of R" may be the same or each may be different, any two or three of R" may be covalently linked to each other; and $R^2$ and $R^3$, independently of one another, can be selected from H, an alkyl group, an aryl group or a substituted alkyl group or a substituted aryl group, where the substituents do not significantly negatively affect the function of the phosphine-borane complex in the Staudinger Ligation, particularly as illustrated in Scheme 2; $R^2$ and $R^3$ may be covalently linked to each other.

In specific embodiments, the invention provides phosphine-borane complexes for use as peptide ligation reagents in which R and R' are alkyl groups, particularly ethyl groups, propyl groups or butyl groups, or aryl groups, particularly phenyl groups or substituted phenyl groups; R" are all H or small alkyl (e.g., methyl, ethyl, propyl, butyl groups); $R^2$ and $R^3$ are H or small alkyl groups (e.g., methyl, ethyl, propyl, butyl groups) and PR is a —CO—$R^5$ group where $R^5$ is H, and alkyl group or an aryl group.

In more specific embodiments, the invention provides phosphine-borane complexes of formula 10 in which R and R' are alkyl groups, particularly ethyl groups, propyl groups or butyl groups; R" are all H or small alkyl (e.g., methyl, ethyl, propyl, butyl groups); $R^2$ and $R^3$ are H and PR is a —CO—$R^5$ group where $R^5$ is H, an alkyl group or an aryl group.

In other specific embodiments, the invention provides phosphine-borane complexes of formula 10 in which R and R' are phenyl groups; R" are all H or small alkyl (e.g., methyl, ethyl, propyl, butyl groups); $R^2$ and $R^3$ are H and PR is a —CO—$R^5$ groups where $R^5$ is H, an alkyl group or an aryl group.

In another aspect, the invention provides phosphine-borane complexes of formula 12:

where R, R', R", R2 and R3 are as defined above and AA is an amino acid, peptide or protein or a fully or partially protected derivative thereof. The AA group can be linked to the thio group of the complex of formula 12 by formation of a thioester at the COOH group of the amino acid (i.e. PRNHC($R^A$)COOH→PRNHC($R^A$)CO-S-C($R_2R_3$)-⊕PRR'-BR"$_3$, where PR an amine protecting group and $R^A$ is an amino acid side-group), at the carboxyl terminus of a peptide or protein (i.e., PRNH-peptide-COOH→PRNH-peptide-CO-S-C($R_2R_3$)-⊕PRR'-BR"$_3$,or at a carboxy group of an amino acid side group $R^A$. Dependent upon where the thioester linkage is formed the AA group can be protected, if needed, with appropriate PR groups at its COOH terminus or at a COOH group on an amino acid side-group. The complex of formula 12 indicates formation of one thioester linkage, however, in cases in which AA is an amino acid with a carboxylate on $R^A$ or a peptide or protein containing one or more $R^A$ containing one or more carboxylates, multiple phosphine-borane complexes in which two or more carboxyl groups (most generally n) of the amino acid or peptide are ligated to the phosphine borane complex of formula 12 can be formed, as illustrated in formula 12d:

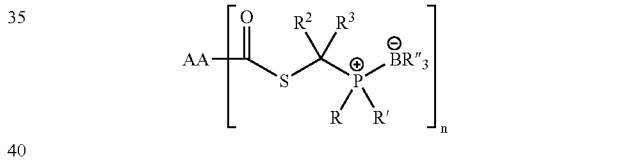

where n is the number of thioesters linkages in the complex, n can be 1, 2, 3, or more. AA can be any naturally-occurring or synthetically prepared amino acid or any naturally-occurring or synthetically-prepared peptide, protein or protein fragment.

In a specific embodiment, AA is a naturally-occurring (D-, L-, achiral or racemic)amino acid and specifically can be selected from the group consisting of any one or more of (D-, L-, achiral or racemic) glycine, alanine, valine, leucine, isoleucine, phenylalanine, serine, methionine, proline, tyrosine, tryptophan, lysine, arginine, histidine, aspartate, glutamate, asparagine, glutamine, cysteine, methionine, hydroxyproline, γ-carboxyglutamate, O-phosphoserine, ornithine, homoarginine and various protected derivatives thereof. Amino acid protecting groups can be selected from any of those known in the art including, but not limited to, Mtr, Pmc, Tos, Mts, Mbh, Tmob, Trt, Xan, tBu, Bzl, OcHEX, Acm, S-tBu, MeBzl, Mob, Bum, Dnp, Bom, Z, CIZ, Boc, CHO or BrZ where conventional abbreviations have been employed to name protecting groups. Those of ordinary skill can select from among the known amino acid protecting groups including those specifically listed, a protecting groups appropriate for a given amino acid and a given moiety within a given amino acid and for a group that is chemically compatible for use in the reactions of this invention.

In additional specific embodiments, the invention provides phosphine-borane complexes of formula 12d where R and R' are alkyl groups or aryl groups which may optionally be substituted and particularly those in which R and R' are both ethyl groups. In other specific embodiments, the invention provides phosphine-borane complexes of formula 12d where $R^2$, $R^3$ are H. In other specific embodiments, the invention provides phosphine-borane complexes of formula 12d where R" are all H or all small alkyl, e.g., methyl or ethyl.

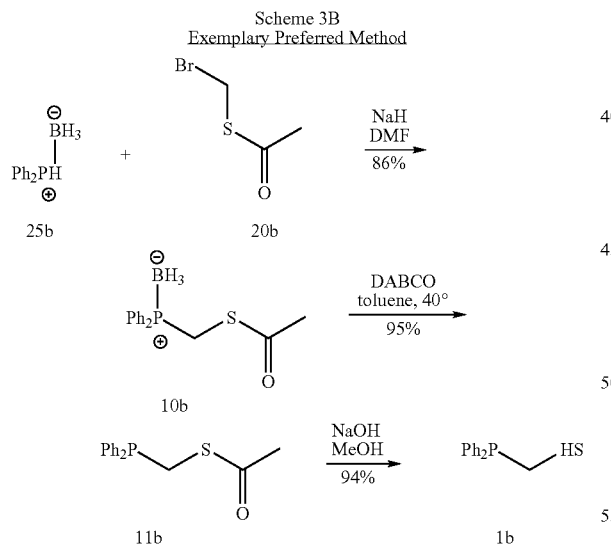

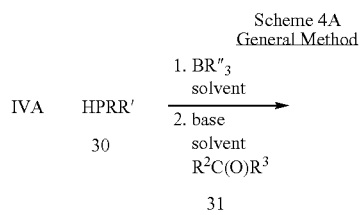

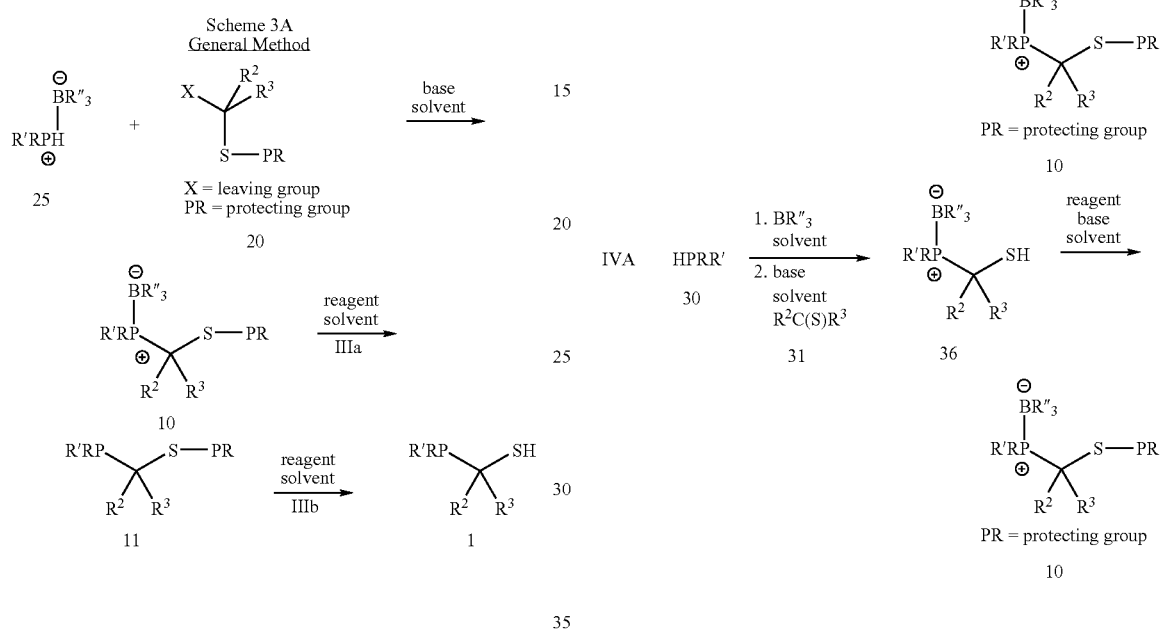

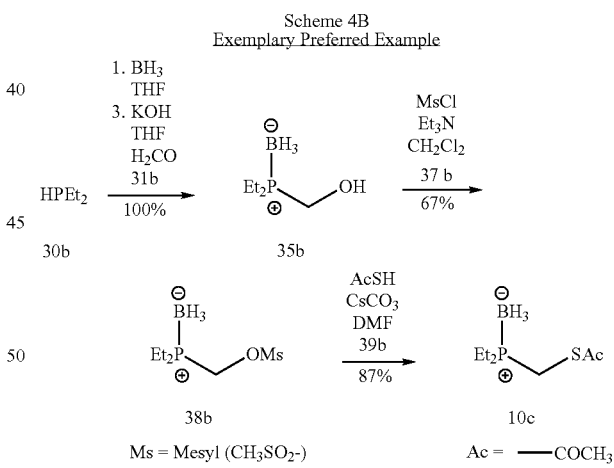

In other specific embodiments, the invention provides phosphine-borane complexes of formula 10 in which R and R' are alkyl groups or phenyl groups; R" are all H; $R^2$ and $R^3$ are H and PR is a —CO—$R^5$ groups where $R^5$ is H, an alkyl group or an aryl group.

The invention further provides kits for the ligation of amino acids, peptides or proteins which comprise one or more phosphine-borane complexes of formula 10, 12 in combination with instructions for carrying out a Staudinger Ligation as illustrated in Scheme 2 or more generally for formation of an amide bond between a thioester and an azide. The phosphine-borane reagents of formula 10, 12 can be provided in one or more suitable containers or receptacles in the kit and may be pre-weighed to provide sufficient reagent for conducting a ligation reaction on a selection scale for a selected amount of starting amino acids, peptide or proteins to be ligated. The kits may additional contain one or more protected amino acid starting materials or other starting materials for ligation. The kit may further contain one or more solvents for conducting the reaction, a deprotecting agent for deprotecting the phosphine-borane complex or other useful reagents or materials useful in the purification of starting materials for ligation or end-products of ligation.

The Staudinger Ligation can be employed generally to form amide bonds. The amide bond is formed between a thioester and an azide and the reaction most generally functions, for any thioester and any azide. In the reaction, the thioester group may be formed, at the carboxy group of an amino acid or at the carboxy terminus of a peptide or protein or at an acid side group of an amino acid or one or more amino acids in a peptide or protein. The azido group may be formed, for example, at the amino group of an amino acid or at the amino terminus of a peptide or protein or at a basic side group of an amino acid or one or more amino acids in a peptide or protein. The reagents of this invention may also be employed to ligate an amino acid, peptide or protein group to a carbohydrate group, which may be a mono-, di-, tri- or polysaccharide, or to a nucleoside. The reagents of this invention may also be employed to ligate an amino acid, a peptide or protein group to a reporter group, tag or label (e.g., a group whose presence can be detected by optical or mass spectrometry or other instrumental method), including a fluorescent or phosphorescent group, an isotopic label or a radiolabel. The invention provides kits comprising one or more phosphine-borane complexes of formula 10, 12 for formation of an amide bond and more specifically for ligation of an amino acid, peptide or protein to a carbohydrate, a nucleoside or to a reporter group, tag or label.

This invention also provides an improved method for forming an amide bond by Staudinger Ligation which employees a phosphine-borane reagent of formula 10, 12.

DETAILED DESCRIPTION OF THE INVENTION

This invention relates generally to improved methods for forming amide bonds and more specifically to improved synthetic methods for forming reagents useful in forming amide bonds and improved reagents for forming amide bonds.

The following terms are defined for use herein:

Alkyl groups refer to saturated hydrocarbon groups which may be linear, branched or cyclic. Small alkyl groups are those having from one to six carbon atoms. Alkyl groups may be substituted so long as the substituents do not significantly detrimentally affect the function of the compound or portion of the compound in which it is found.

Aryl groups refer to groups which contain at least one aromatic ring which can be a five-member or a six-member ring. The one or more rings of an aryl group can include fused rings. Aryl groups may be substituted with one or more alkyl groups which may be linear, branched or cyclic. Aryl groups may also be substituted at ring positions with substituents that do not significantly detrimentally affect the function of the compound or portion of the compound in which it is found. Substituted aryl groups also include those having heterocyclic aromatic rings in which one or more heteroatoms (e.g., N, O or S, optionally with hydrogens or substituents for proper valence) replace one or more carbons in the ring.

Scheme 3A provides a generalized method for synthesis of a phosphinothiol reagent (1) of this invention. The synthesis is based on the reaction of an alkylating agent 20 and a borane-organophosphine complex 25. The phosphine of the phosphine-borane complex 25 is deprotonated with base followed by alkylation with 20 to give phosphine-borane complex 10. Phosphine-borane complexes 10 are stable to air and moisture and can be stored at room temperature for months without any sign of oxidation or decomposition.

The borane complex 10 is disrupted by mild heating, in the presence of an amine, preferably with DABCO in toluene for 4 hr to generate a protected phosphinothiol 11 (PR in this case should be resistant to deprotection under the conditions of complex disruption IIIa). A preferred protecting group is an —CO—$R^5$ group, particularly an acyl group, which can be removed as previously described[4b] to give the phosphinothiol 1. The use of and methods for removal of other suitable protecting groups is known in the art.

Useful bases for deprotonation of the phosphine-borane complex 25 in the first step of the synthesis of Scheme 3A are NaH, LiH, KH, KOtBu, NaOMe, NaOEt and the use of NaH is preferred. Amine bases are not preferred, as they can remove the $BH_3$ protecting group. While DMF is a preferred solvent for this first step, other useful solvents include THF, toluene, DMA and more generally any solvent that will dissolve the various components and not significantly detrimentally affect the desired reaction. Solvents including thiols, thioethers, and amines should not be used.

The preferred reagent for disrupting the borane complex 10 is DABCO (1,4-diazabicyclo[2.2.2]octane), but primary, secondary, tertiary or aromatic amines, thiols or thioethers can also be used in this step. Amines such as pyridine, N,N,N',N'-tetra-methylethylenediamine, diethylamine, triethylenediamine, or dimethylsulfide can specifically be used. The preferred solvent for this step is toluene, but benzene, THF, or any solvent that will dissolve the reagents can be used.

The protecting group of the acyl phosphinothiol can be removed by reaction with base in alcohol. Preferred deprotection agent is 1 eq. NaOH in MeOH. Other reagents include excess NaOH, (1 equivalent or excess) LiOH, KOH, $NH_3$, $NH_2OH$ $NaHCO_3$ in $H_2O$/THF, $LiAlH_4$ in ether, $AgNO_3$ in MeOH or a lipase enzyme. Methanol is the preferred solvent, but other alcohols (including EtOH, iPrOH) or $H_2O$ can be employed. Oxygen gas should be removed from the solvent to prevent oxidation of the phosphene to a phosphene oxide. DMSO should be avoided as a solvent in this step The protecting group of the acyl phosphinothiol can be removed by reaction with base in alcohol. Preferred deprotection agent is 1 eq. NaOH in MeOH. Other reagents include excess NaOH, (1 equivalent or excess) LiOH, KOH, $NH_3$ or $NH_2OH$. Methanol is the preferred solvent, but other alcohols (including EtOH, iPrOH) or $H_2O$ can be employed. $O_2$ (g) should be removed from the solvent to prevent oxidation of phosphene to a phosphene oxide. DMSO should be avoided as a solvent in this step.

Scheme 3B illustrates the synthesis of a specific phosphinothiol 1b where R and R' are both phenyl groups and $R^2$ and $R^3$ are both hydrogens. The illustrated synthesis of Scheme 3B gave an overall yield of about 74%. See the Examples for experimental details.

With respect to starting reagents in Scheme 3A, R and R' can generally be any organic moiety (including alkyl and aryl) that does not contain an amine, thiol or thioether. The R' and R groups can be linked to P via a C—P or O—P bond. More specifically, R' and R are optionally substituted alkyl group alkoxide group, aryl group or aryloxy group. Alkyl groups include straight-chain, branched or cyclic alkyl groups. Aryl groups may contain one or more (preferably one or two) aromatic rings which may be carbocyclic or heterocylic rings. Preferred alkyl groups are optionally substituted ethyl groups. Preferred alkoxy groups are ethoxy groups. Preferred aryl groups are optionally substituted phenyl groups including phenyl groups and halogen (particularly fluorine)-substituted or carboxy-substituted phenyl groups.

Various known protecting groups (PR) can be employed in the starting reagents of Scheme 3A. One or ordinary skill in the art in view of the teachings herein and what is well-known in the art can selected appropriate protecting groups from those available in the art. Preferred protecting groups are —CO—$R^5$ groups where R5 is hydrogen, alkyl, aryl or substituted alkyl or substituted aryl groups ($R^5$ can specifically be hydrogen, methyl, ethyl or other small alkyl group, a —$CH_2$—Ph group (Ph=phenyl), a —$CH_2$—Ph$(Y)_n$ group where Y is a substituent and n is the number of substituents (Y can, for example, be a halogen, including fluorine, or —$OR^7$ where $R^7$ is an optionally substituted alkyl or aryl group.)

In all cases, optional substituents include halogens and alkoxy groups and for appropriate groups can be alkyl, and or aryl substituents. Optional substituents do not include amines, thiols or thioester groups.

In Scheme 3A in the thioester reagent is a "good leaving group", as that term is generally known and accepted in the art, that does not include an amine, a thiol or a thioether group. Preferred X are halogens (Br, Cl or I), OTs (tosyl, $CH_3C_6H_4SO_2$—), OTf (triflate, $CF_3SO_2$—), or OMs (mesyl, $CH_3SO_2$—). The most preferred X is Br.

The leaving group X is preferably separated from S by a —$CR^2R^3$— group, e.g., —$CH_2$— where $R^2$ and $R^3$ are both hydrogens, as illustrated in Schemes 3A and 3B. However, the linker to S can also be —$CH_2$—$CH_2$— or an o-substituted Phe group as in

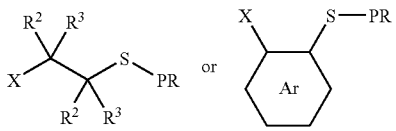

where $R^2$ and $R^3$ groups, independent of other $R^2$ and $R^3$ groups in the same molecule, are as defined above and where Ar is an optionally substituted aryl group which may contain one or more aromatic rings. PR is preferably an acyl group, e.g., a —$COR^5$ group as defined above.

Starting materials and reagents for the reactions of Scheme 3A are readily available either from commercial sources, by use of known synthetic methods or by routine adaptation of known synthetic methods.

Scheme 4A provides two related generalized methods for synthesis of protected reagents 10 of this invention. The synthesis is based on the addition of an aldehyde or ketone (31) to a phosphine-borane complex (not specifically shown) to form the phosphine-borane complex alcohol 35. The phosphine of the initial phosphine-borane complex formed is deprotonated with base followed by addition of the aldehyde or ketone to give the derivatized alcohol phosphine-borane complex 35. The alcohol-containing phosphine-borane complex (35) is activated by introduction of an activating group A by reaction with AX (37). The alcohol is activated for reaction with a protected thiol (39), such as an acyl thiol, particularly thioacetic acid to form the phosphine-borane complex 10. Complexes 10 are stable to air and moisture and can be stored at room temperature for months without any sign of oxidation or decomposition.

Alternatively, reaction IVB can be used to directly prepare complex 10 by replacing aldehyde or ketone 31 with the sulfur analogs 32.

The borane complex 10 can be disrupted by mild heating, in the presence of an amine, preferably with DABCO in toluene to generate a protected phosphinothiol 11 (PR in this case should be resistant to deprotection under the conditions of complex disruption). A preferred protecting group is an acyl group, e.g., a —CO—$R^5$ group, particularly an acetyl group, which can be removed as described in references 4a and b to give a phosphinothiol of formula 1 which can be employed as illustrated in Scheme 3A in the Staudinger Ligation to form a thioester. The use of and methods for removal of other suitable protecting groups is known in the art.

However, rather than generating the phosphinothiol 1, complex 10 can be used to generate derivatized amino acid, peptide or protein reagents of formula 12, which can be employed in the Staudinger Ligation as illustrated in Scheme 2. The complex of formula 10 is coupled with an amino acid, peptide or protein that is activated by incorporation of a good leaving group LG. The amino acid, peptide or protein of the complex of formula 12 is provided with appropriate protecting groups to allow the reaction to proceed as indicated in the first reaction of Scheme 2. It has been found that derivatized amino acid, peptide or protein complexes of formula 12, on disruption of the phosphine-borane complex, react with azides as indicated in Scheme 2. Scheme 2 illustrates the Staudinger Ligation to form a n amide bond between two peptides. Complexes of formula 12d can also be employed to form amide bonds between any two of an amino acid, peptide or protein. Complexes of formula 12d can further be employed to form an amide bond between an amino acid, a peptide or a protein and a carbohydrate, a nucleoside or a suitable reporter, tag or label.

The method of Scheme 2 is preferred for use with phosphinothiols that are unstable, for example those in which R and R' are ethyl groups.

Amine bases are not preferred, for use in the reactions of Schemes 2 and 4A, unless otherwise stated, as they can remove the $BH_3$ protecting group. In additional to the preferred base KOH, for formation of complexes 35 and 36, other bases including NaH, LiH, KH, KOtBu, NaOMe, and NaOEt can be used. While THF is a preferred solvent for this reaction, other useful solvents include THF, toluene, DMA and more generally any solvent that will dissolve the various components and not significantly detrimentally affect the desired reaction. Solvents including thiols, thioethers, and amines should not be used in the reactions of Schemes 2 and 4A, unless otherwise indicated.

The preferred reagent for disrupting the phosphine-borane complexes is DABCO (1,4-diazabicyclo[2.2.2]octane), but primary, secondary, tertiary or aromatic amines, thiols or thioethers can also be used in this step. Amines such as pyridine, N,N,N',N'-tetra-methylethylenediamine, diethylamine, triethylenediamine, or dimethylsulfide can specifically be used. The preferred solvent for this step is toluene, but benzene, THF, or any solvent that will dissolve the reagents can be used.

The protecting group of the protected complex 10 can be removed, if desired, for example by reaction with base in alcohol. Other reagents include excess NaOH, (1 equivalent or excess) LiOH, KOH, $NH_3$, $NH_2OH$ $NaHCO_3$ in $H_2O$/THF, $LiAlH_4$ in ether, $AgNO_3$ in MeOH or a lipase enzyme. Oxygen gas should be removed from the solvent to prevent oxidation of the phosphene to a phosphene oxide.

Scheme 4B illustrates the synthesis of a specific phosphine-borane complex 10c where R and R' are both ethyl groups and $R^2$ and $R^3$ are both hydrogens.

As noted above complexes of formula 12 and 12d can be employed as illustrated, for example, in Scheme 2 to form amide bonds between amino acids, peptides or proteins or between an amino acid and another species, such as a carbohydrate (e.g., a saccharide) a nucleoside or simply to an appropriate reporter group, tag or label. If desired, the complex 12 or 12d can be disrupted as illustrated in Scheme 2 (page 2) employing DABCO or other amine.

Starting materials and reagents for the reactions of Scheme 4A are readily available either from commercial sources, by known synthetic methods or routine adaptation of known synthetic methods.

Several non-glycyl α-azido acids were prepared to examine epimerization during the Staudinger ligation. The azido benzamides of both the D and L enantiomers of phenylalanine, serine, and aspartic acid were prepared (Scheme 5). The azido group was prepared by diazo transfer;[10] the benazmide was prepared by DCC/HOBt coupling with benzyl amine. Phenylalanine, aspartic acid, and serine were chosen as being representative of three distinct side chains and moderate (phenylalanine) to high (aspartate and serine) propensity to epimerize during standard peptide couplings.[16]

Each of these azido acids was coupled with phosphinothioester 51 (which is $AcGlySCH_2PPh_2$;Table 1). The couplings were carried out in $THF/H_2O$ (3:1) for 12 h at room temperature with a 1:1 stoichiometry of starting materials. The resulting peptides were purified by flash chromatography to give a nearly quantitative yield of each product (Table 1). The high yield of this equimolar reaction of phosphinothiol 1 with non-glycyl azides is consistent with those observed previously[4b]. The preparation of phosphinothioester 51 was modified from that described in references 4a and b in which coupling using DCC alone led to lower yields and several undesired side products. Pretreatment of N-acetyl glycine with HOBt and DCC followed by addition of the phosphinothiol 1 improved the yield dramatically. See the Examples.

The chirality of the Staudinger Ligation products from the reaction of the D and L α-azido acids was analyzed by HPLC using a D-phenylglycine chiral column. The chromatographic conditions enabled the baseline resolution of the two possible enantiomeric products (FIG. 1). Materials to be analyzed were injected onto a D-phenylglycine analytical HPLC column and eluted with 30% (v/v) isopropanol in hexanes (isocratic0 for 20 min followed by a shallow gradient to 50% (v/v) isopropanol for 40 min. After reaction of the D epimer, there was no evidence of product containing the L epimer, and vice versa. Thus, the Staudinger Ligation proceeds without detectable epimerization of the α-carbon of the azido acid. The detection limit of the HPLC chromatographic analysis used is estimated to be ≦0.5%, so that the Staudinger Ligation proceeds with ≧99.5% retention of chirality.

Those or ordinary skill in the art will appreciate that starting materials, reagents, solvents, temperature and other reaction conditions other than those specifically disclosed, can be employed in the practice of this invention without resort to undue experimentation. All such art-recognized equivalents are included to be encompassed by this invention. All references cited herein are incorporated by reference in their entirety. In particular, published PCT application WO 01/87920 is cited herein and incorporated by reference herein to provide details of the Stauding Ligation and method for amide bond formation using the phosphinothiol reagents (1) and the phosphine-borane complexes 10, 12 and 12d.

THE EXAMPLES

Amino acids were from NovaBiochem (San Diego, Calif.) and all other chemicals and solvents were from Aldrich (Milwaukee, Wis.). Reactions were monitored by thin-layer chromatography using Whatman TLC plates (AL SIL G/UV) with visualization by UV light or staining with ninhydrin or $I_2$. Silica gel used in flash chromatography was obtained from SiliCycle (Quebec, Canada). Chiral HPLC was performed with a D-phenylglycine analytical chiral column from MetaChem (Torrance, Calif.). NMR spectra were obtained with a Varian INOVA-500 MHz spectrometer or a Bruker AC-300 300 MHz spectrometer at the University of Wisconsin nuclear magnetic resonance facility. Carbon-13 and phosphorus-31 NMR spectra were both proton-decoupled and phosphorus-31 spectra were referenced against an external standard of deuterated phosphoric acid (0 ppm). Mass spectra were obtained with electrospray ionization (ESI) techniques on a Micromass LCT instrument.

Borane-thioacetic acid
S-[(diphenylphosphanyl)-methyl] ester complex
(10b)

Borane-diphenylphosphine complex 25b (10.33 g, 51.6 mmol) was dissolved in dry DMF under Ar(g) and cooled to 0° C. NaH (1.24 g, 51.6 mmol) was added slowly, and the mixture was stirred at 0° C. until bubbling ceased. Alkylating agent 20b[13] (8.73 g, 51.6 mmol) was then added, and the mixture was allowed to warm to room temperature and stirred for 12 h. Solvent was removed under reduced pressure, and the residue was purified by flash chromatography (silica gel, 10% v/v EtOAc in hexanes). Compound 10b was isolated as a colorless oil in 86% yield. Spectral data. $^1H$ NMR (300 MHz, $CDCl_3$) δ 7.74-7.67 (m, 4H), 7.54-7.41 (m, 6H), 3.72 d, J=6 Hz, 2H), 2.23 (s, 3H), 1.51-0.53 (broad m, 3H) ppm; $^{13}C$ NMR (75 MHz, $CDCl_3$) δ 192.94, 132.26 (d, J=9.2 Hz), 131.61 (d, J=2.3 Hz), 128.71 (d, J=10.2 Hz), 127.43 (d, J=55.4 Hz), 29.87, 23.59 (d, J=35.5. Hz) ppm; $^{31}P$ NMR (121 MHz, $CDCl_3$) 19.40 (d, J=59.3 Hz) ppm; MS (ESI) m/z 311.0806 ($MNa^+[C_{15}H_{18}BOPSNa]$=311.0807).

Thioacetic acid S-[(diphenylphosphanyl)-methyl] ester (11b). Compound 10b (4.00 g, 13.9 mmol) was dissolved in toluene (0.14 L) under Ar(g). DABCO (1.56 g, 13.9 mmol) was added, and the mixture was heated at 40° C. for 4 h. Solvent was removed under reduced pressure, and the residue was dissolved in $CH_2Cl_2$ and washed with both 1 N HCl and saturated brine. The organic layer was dried over $MgSO_4$(s), and the solvent was removed under reduced pressure. Compound 1b was isolated in 95% yield, and was used without further purification. Spectral Data. As reported previously.[4b]

(Diphenylphosphino)methanethiol (1b). Compound 11b (17.27 g, 63.0 mmol) was dissolved in anhydrous methanol and Ar(g) was bubbled through the solution for 1 h. Sodium hydroxide (2.52 g, 63 mmol) was then added, and the mixture was stirred under Ar(g) for 2 h. Solvent was then removed under reduced pressure, and the residue was dissolved in methylene chloride. This solution was washed twice with 2 N HCl and once with brine. The organic layer was dried over $MgSO_4$(s) and filtered, and the solvent was removed under reduced pressure. The residue was purified by chromatography (alumina, 25% v/v ethyl acetate:hexanes) to afford 1b as a clear oil in 94% yield. Alternatively, phosphinothiol 1b can be used in its crude form for formation of phosphinothioesters. Spectral data. $^1$H NMR ($CDCl_3$, 300 MHz) δ 7.41-7.38 (m, 4H), 7.33-7.26 (m, 6H), 3.02 (d, J=7.8 Hz, 2H), 1.38 (t, J=7.5 Hz, 1H) ppm; $^{13}$C NMR ($CDCl_3$, 75 MHz) δ 132.54 (d, J=17.1 Hz), 128.86, 128.36, 128.14, 20.60 (d, J=21.7 Hz) ppm; $^{31}$P NMR ($CDCl_3$, 121 MHz) 6-7/94 ppm; MS (ESI) m/z 232.05 ($MH^+$=233.0, fragments at 183.0, 155.0, 139.0, 91.2).

2(S)-Azido-N-benzyl-3-phenyl-propionamide (48-L). $N_3$(L)PheOH (1SL) was synthesized from L-phenylalanine essentially by the procedure of Lundquist and Pelletier.[17] $N_3$(L)PheOH (1.08 g, 5.7 mmol) was dissolved in anhydrous DMF (40 mL). HOBt (0.87 g, 5.7 mmol) was then added, followed by DCC (1.17 g, 5.7 mmol). Once precipitate was observed in the reaction, benzyl amine (0.62 mL, 5.7 mmol) was added. The reaction was allowed to stir under Ar(g) for 3 h. The resulting precipitate (DCU) was removed by filtration, and the filtrate was concentrated under reduced pressure to give a yellow oil. This oil was purified by flash chromatography (silica gel, 35% v/v/ethyl acetate in hexanes). $N_3$(L)Penh (48-L) was isolated as an off-white solid in 90% yield. The procedure was repeated with D-phenylalanine to give $N_3$(D)Penh products (D and L enantiomers) are identical. $N_3$(L)Penh (48-L) $^1$H NMR (500 MHz, $CDCl_3$ δ 7.31-7.12 (m, 8H), 7.11 (m, 2H), 6.55 (bus, 1H), 4.38 (m, 2H), 4.22 (did, J=7.8, 4.6 Hz, 1H), 3.34 (did, J=14.0, 4.5 Hz, 1H), 3.07 (did, J=14.1, 7.5 Hz, 1H) ppm; $^{13}$C NMR (125 MHz, $CDCl_3$) δ 168.30, 137.35, 135.96, 129.51, 128.61, 128.66, 128.61, 128.55, 127.70, 127.68, 127.66, 127.57, 127.16, 65.40, 43.41, 38.41 ppm; MS (ESI) m/z 303.1235 ($MNa^+$[$C_{16}H_{16}N_4ONa$]=303.1222).

3(S)-Azido-N-benzyl-succinamic acid methyl ester (49-L). Benzyl-protected L-aspartate was used in the procedure of Lundquist and Pelletier[17] to give $N_3$(L)Asp(OMe)OH (46-L). Under these conditions, we observed transesterification to give the methyl ester product as opposed to the benzyl ester. $N_3$(L)Asp(OMe)OH (46-L) was produced as a yellowish oil in 78% yield. $N_3$(L)Asp(OMe)OH (46-L) was then coupled with benzylamine as above to give $N_3$(L)Asp(OMe)NHBn (49-L) as a yellowish oil in 90% yield (70% overall, two steps). The procedure above was repeated with benzyl-protected D-aspartate to give $N_3$(L)Asp(OMe)NHBn (49-D) as a yellowish oil in 67% overall yield. Spectral Data. The spectral data for both $N_3$Asp(OMe)OH (D and L enantiomers) and both $N_3$Asp(OMe)NHBn (D and L enantiomers) products are identical. $N_3$(L)Asp(OMe)OH (46-L) $^1$H NMR (500 MHz, $CDCl_3$) δ 10.24 (bs,1H), 4.47 (dd, J=7.4, 5.3 Hz, 1H), 3.76 (s, 3H), 2.91 (dd, J=16.9, 5.1 Hz, 1H), 2.79 (dd, J=16.8, 7.6 Hz) ppm; $^{13}$C NMR (125 MHz, $CDCl_3$) δ 174.68, 170.12, 50.09, 52.44, 35.84 ppm; MS (ESI) m/z 196.0340 ($MNa^+$[$C_5H_7N_3O_4Na$]=196.0334). $N_3$(L)Asp(OMe)NHBn (49-L) $^1$H NMR (500 MHz, $CDCl_3$) δ 7.38-7.27 (m, 5H), 6.83 (bs, 1H), 4.54 (m, 3H), 3.75 (s, 3H), 3.18 (dd, J=17.1, 3.7 Hz, 1H), 2.75 (dd, J=17.3, 8.7 Hz, 1H) ppm; $^{13}$C NMR (125 MHz, $CDCl_3$) δ 170.77, 167.90, 137.35, 128.81, 127.80, 127.77, 60.32, 52.24, 43.71, 37.00 ppm; MS (ESI) m/z 285.0953 ($MNa^+$[$C_{12}H_{12}N_4O_3Na$]=285.0964).

2(S)-Azido-N-benzyl-3-benzyloxy-propionamide (50-L)

Benzyl-protected L-serine was used in the procedure above to give $N_3$(L)Ser(Bzl)NHBn (50-L) as a yellowish oil in 93% yield. The procedure was repeated with benzyl-protected D-serine to give $N_3$(D)Ser(Bzl)NHBn (50-D) as a yellowish oil in 90% yield. Spectral data. The spectral data for both $N_3$Ser(Bzl)NHBn products (D and L enantiomers) are identical. $N_3$(L)Ser(Bzl)NHBn (50-L) $^1$H NMR (500 MHz, $CDCl_3$) δ 7.36-7.23 (m, 10H), 6.86 (bs, 1H), 4.57 (s, 2H), 4.43 (m, 2H), 4.25 (dd, J=6.9, 3.5 Hz, 1H), 4.01 (dd, J=10.3, 3.5 Hz, 1H), 3.83 (10.1, 6.7 Hz, 1H), ppm; $^{13}$C NMR (125 MHz, $CDCl_3$) δ 166.81, 137.40, 137.22, 128.65, 128.40, 127.81, 127.59, 127.54, 73.45, 70.54, 63.28, 43.38 ppm; MS (ESI) m/z 333.1337 ($MNa^+$[$C_{17}H_{18}N_4O_2Na$]= 333.1327).

Acetylamino-thioacetic acid S-[(diphenylphosphanyl)-methyl] ester (51). N-Acetylglycine (1.90 g, 16.2 mmol) was dissolved in anhydrous DMF (75 mL). HOBt (2.48 g, 16.2 mmol) was added to the resulting solution followed by DCC (3.34 g, 16.2 mmol). Once precipitate (DCU) was observed, phosphinothiol 1b was added (3.77 g, 16.2 mmol). The reaction mixture was allowed to stir under Ar(g) for 3 h. The precipitate was removed by filtration, and the filtrate was concentrated under reduced pressure to give a white solid. This solid was dissolved in ethyl acetate and purified by flash chromatography (silica gel, ethyl acetate). Compound 51 was isolated in 96% yield. Spectral Data. As reported previously 2(S)-(2-Acetylamino-acetylamino)-N-benzyl-3-phenyl-propionamide (52-L). N-Acetylglycylphosphinothioester 9 (0.166 g, 0.5 mmol) and $N_3$(L)PheNHBn (18-L) (0.140 g, 0.5 mmol) was dissolved in THF/$H_2O$ (3:1, 4 mL), and the mixture was stirred at room temperature for 12 h. Solvent was removed under reduced pressure, and the residue was purified by flash chromatography (silica gel, 5% v/v methanol in dichloromethane). AcGly(L)PheNHBn (52-L) was obtained as a white solid in 90% yield. The procedure was repeated with $N_3$(D)PheNHBn (48-D) to give AcGly(D) PheNHBn (22-D) in 93% yield. Spectral Data. The spectral data for both dipeptide products (D and L enantiomers) are identical.

AcGly(L)PheNHBn (52-L) $^1$H NMR (300 MHz, $CDCl_3$: $CD_3OD$ 1:1) δ 7.30-7.22 (m, 6H), 7.19-7.16 (m, 2H), 7.16-7.11 (m, 2H), 4.63 (t, J=7.3 Hz, 1H), 4.33 (dd, J=31.1, 14.6 Hz, 2H), 3.79 (dd, J=33.1, 16.7 Hz, 2H), 3.12 (dd=J 13.8, 7.2 Hz, 1H), 2.98 (dd, J=13.7, 7.2 Hz, 1H), 1.98 (s, 3H) ppm; $^{13}$C NMR (125 MHz, $CDCl_3$:$CD_3OD$ 1:1) δ 171.98, 170.93, 169.33, 137.29, 136.00, 128.76, 128.05, 127.97, 127.03, 126.75, 126.41, 54.16, 42.79, 42.37, 37.52, 21.56 ppm; MS (ESI) m/z 376.1624 ($MN^+$[$C_{20}H_{23}N_3O_3Na$]= 376.1637).

3(S)-(2-Acetylamino-acetylamino)-N-benzyl-succinamic acid methyl ester (53-L)

$N_3$(L)Asp(OMe)NHBn (49-L) was used in the procedure above to give AcGly(L)Asp(OMe)NHBn (53-L) as a white solid in 91% yield. The procedure was repeated with $N_3$(D) Asp(OMe)NHBn (49-D) to give AcGly(D)Asp(OMe)NHBn (53-D) as a white solid in 95% yield. Spectral Data. The spectral data for both AcGlyAsp(OMe)NHBn products (D and L enantiomers) are identical. AcGly(L)Asp(OMe)NHBn (53-L) $^1$H NMR (500 MHz, CDCl$_3$:CD$_3$OD 1:1) δ 7.34-7.23 (m, 5H), 4.84 (t, J=5.7 Hz, 1H), 4.34 (s, 2H), 3.84 (q, J=16.6 Hz, 2H), 3.69 (s, 3H), 2.87 (m, 2H), 2.01 (s, 3H) ppm; $^{13}$C NMR (125 MHz, CDCl$_3$:CD$_3$OD 1:1) δ 177.24, 176.43, 175.18, 174.58, 142.56, 133.17, 133.03, 131.93, 131.78, 56.46, 54.13, 47.91, 47.81, 47.67, 40.11, 26.59 ppm; MS (ESI) m/z 358.1388 (MNa$^+$[C$_{16}$H$_{21}$N$_3$O$_5$Na]=358.1379).

2(S)-(2-Acetylamino-acetylamino)-N-benzyl-3-benzyloxy-propionamide (54-L)

N$_3$(L)Ser(Bzl)NHbn (50-L) was used in the procedure above to give AcGly(L)Ser(Bzl)NHBn (54-L) as a white solid in 92% yield. The procedure was repeated with N$_3$(D) PheNHBn (50-D) to give AcGly(D)Ser(Bzl)NHBn (54-D) as a white solid in 99% yield. Spectral Data. The spectral data for both AcGlySer(Bzl)NHBn products (D and L enantiomers) are identical. AcGly(L)Ser(Bzl)NHBn (54-L) $^1$H NMR (500 MHz, CDCl$_3$:Cd$_3$OD 1:1) δ 7.34-7.21 (m, 10H), 4.60 (t, J=4.4 Hz, 1H), 4.43 (dd, J=23.9, 14.9 Hz, 2H), 3.85 (m, 3H), 3.69 (dd, J=9.6,4.6 Hz, 1H), 1.98 (s, 3H) ppm; $^{13}$C NMR (125 MHz, CDCl$_3$:CD$_3$OD 1:1) δ 172.19, 169.86, 169.61, 137.49, 127.87, 127.31, 127.23, 127.76, 126.59, 72.88 69.07, 52.93, 42.71, 42.49, 21.38 ppm; MS (ESI) m/z 406.1750 (MNa$^+$[C$_{21}$H$_{25}$N$_3$O$_4$Na]=406.1743.

Synthesis of 35b:

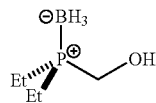

To a solution of borane dimethylsulfide complex (10M in THF, 2.5 mL) in freshly distilled tetrahydrofuran (10 mL) was added diethylphosphine (30b, 2 mL, 17.45 mmol). The solution was stirred under nitrogen for 2 hours. The reaction was carefully quenched with ice, and then extracted with ethyl acetate (3×10 mL). The combined organic layers were washed with brine (2×10 mL), dried with magnesium sulfate, filtered and concentrated. The crude phosphine-borane complex was dissolved in a mixture of tetrahydrofuran (10 mL) and aqueous formaldehyde (37%, 10 mL). Potassium hydroxide (1 g, 17.86 mmol) was added to the solution, and kept stirring under nitrogen for 4 hours. The volatile solvent was removed under vacuum, and the aqueous solution was extracted with ethyl acetate (2×10 mL). The combined organic layers were washed with brine (3×10 mL), dried with magnesium sulfate, filtered and concentrated. The residue was purified with flash chromatography (2:1 hexanes:ethyl acetate) to yield the alcohol (35b) as colorless oil (2.34 g, 100% yield over 2 steps). $^1$H NMR (CDCl$_3$) 3.96 (s, 2H), 1.63-1.76 (m, 4H), 1.10-1.18 (m, 6H), −0.13-0.77 (m, 3H) $^{31}$P NMR (CDCl$_3$) 23 (q, J=56.7 Hz).

Synthesis of 38b:

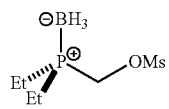

A solution of the alcohol 35b (743 mg, 5.58 mmol) and triethylamine (1.2 mL, 8.6 mmol) in freshly distilled methylene chloride (10 mL) was cooled to 0° C. To this solution, mesyl chloride 37b (600 μL, 7.75 mmol) was added, and the mixture was stirred under nitrogen for over night. The solution was washed with water (2×5 mL), HCl (0.5M, 5 mL) and water (5 mL). The organic layer was dried with magnesium sulfate, filtered and concentrated. The residue was purified by flash chromatography (3:1 hexanes:ethyl acetate) to yield the mesylate 38b as pale yellowish oil (794 mg, 67% yield). $^1$H NMR (CDCl$_3$) 4.46 (d, J=1.8 Hz, 2H), 3.07 (s, 3H), 1.49-1.84 (m, 4H), 1.11-1.22 (m, 6H), −0.13-0.75 (m, 3H) $^{31}$P NMR (CDCl$_3$) 26.08 (q, J=42.8 Hz).

Synthesis of 10c:

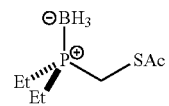

The mesylate 38b (228 mg, 1.04 mmol) was dissolved in dry amine-free N,N-dimethylformamide (2 mL), followed by addition of thioacetic acid 39b (85 μL, 1.19 mmol). The solution was cooled to 0° C. and cesium carbonate (340 mg, 1.04 mmol) was added. After stirring under nitrogen for over night, the dark colored solution was filtered and concentrated. The residue was purified by flash chromatography (3:1 hexanes:ethyl acetate) to yield the thiolacetate 10c as slightly yellowish oil (174 mg, 87% yield). $^1$H NMR (CDCl$_3$) 6.31 (d, J=6 Hz, 2H), 2.40 (s, 3H), 1.66 (dq, J=10.2, 7.6 Hz, 4H), 1.14 (dt, J=16.1, 7.9 Hz, 6H), −0.04-0.86 (m, 3H) $^{13}$C NMR 193.44, 30.23, 20.28 (d, J=112.27 Hz), 15.49 (d, J=141.00 Hz), 3.66 (d, J=9.6 Hz) $^{31}$P NMR (CDCl$_3$) 25.92 (q, J=47.6 Hz).

Synthesis of compound of formula 12d:

63

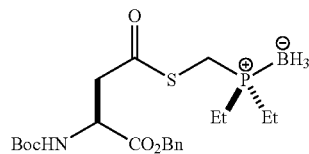

The thiolacetate 10c (190 mg, 1 mmol) was dissolved in methanol (5 mL), followed by addition of sodium methoxide solution (1M in methanol, 1 mL). The solution was stirred under nitrogen for 10 minutes. The solution was neutralized by pH 6.5 phosphate buffer, extracted with ethyl acetate (2×5 mL). The combined organic layers were washed with brine (2×5 mL), dried with sodium sulfate, filtered and concentrated. The crude product was dissolved in freshly distilled methylene chloride (5 mL) with Boc-Asp-OBzl (323 mg, 1 mmol), a protected amino acid. To this solution, catalytic DMAP (2 mg) and DCC (206 mg, 1 mmol) were added. The solution was kept stirring under nitrogen for 2 hours. The volatile solvent was removed under vacuum and the residue was purified by flash chromatography (3:1 hexanes:ethyl acetate) to yield the thiolester 63 as colorless oil (430 mg, 95.4% yield over two steps). $^1$H NMR (CDCl$_3$) 7.31 (m, 5H) 5.44 (d, J=7.5 Hz, 1H), 5.14 (s, 2H), 4.57 (m, 1H), 3.20 (broad s, 2H), 3.08 (d, J=6 Hz), 1.59 (qt, J=6.9 Hz, 4H), 1.40 (s, 9H), 1.07 (dt, J=16.2, 8.4 Hz), −0.26-0.51 (m, 3H) $^{13}$C NMR (CDCl$_3$) 234.85, 194.66, 170.24, 134.93, 128.49, 128.42, 129.19, 80.26, 67.55, 50.52, 28.15, 20.07 (d, J=28 Hz), 15.34 (d, J=35.6 Hz), 6.55 (d, J=2.4 Hz) $^{31}$P NMR (CDCl$_3$) 26.17 (d J=142.8 Hz).

Synthesis of phosphinolthiol of formula 1:

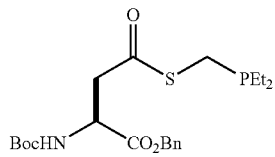

The phosphine-borane complex 63 (170 mg, 0.373 mmol) and DABCO (84 mg, 0.75 mmol) were dissolved in freshly distilled toluene. The solution was heated under argon at 80° C. for 2 hours. The solution was cooled to room temperature and filtered through a plug of silica gel under nitrogen. The phosphinothiolester 64 was collected as an oil (131 mg, 80% yield). $^1$H NMR (CDCl$_3$) 7.35 (m, 5H), 5.44 (d, J=9.3 Hz, 1H), 5.19 (s, 2H), 4.59 (m, 1H), 3.18-3.25 (m, 2H), 3.01 (d, J=5.4 Hz, 2H), 1.44 (m, 13H), 1.05 (dt, J=18.6, 9.3 Hz, 6H). Due to the instability of this compound, no $^{13}$C NMR was performed.

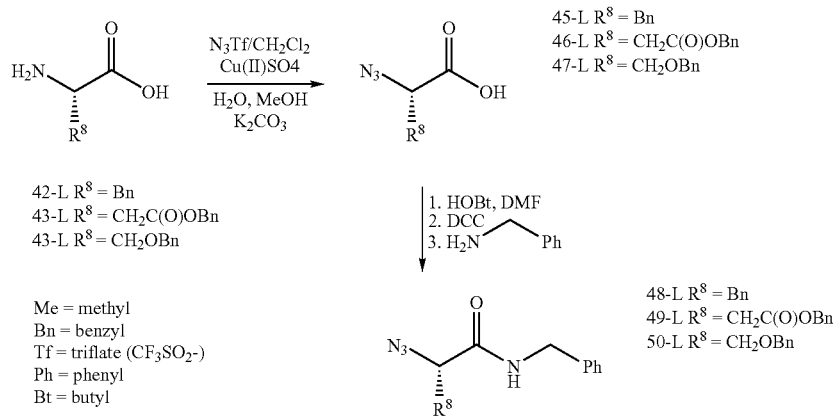

SCHEME 5

45-L R$^8$ = Bn
46-L R$^8$ = CH$_2$C(O)OBn
47-L R$^8$ = CH$_2$OBn

42-L R$^8$ = Bn
43-L R$^8$ = CH$_2$C(O)OBn
43-L R$^8$ = CH$_2$OBn

48-L R$^8$ = Bn
49-L R$^8$ = CH$_2$C(O)OBn
50-L R$^8$ = CH$_2$OBn

Me = methyl
Bn = benzyl
Tf = triflate (CF$_3$SO$_2$-)
Ph = phenyl
Bt = butyl

TABLE 1

Staudinger Ligation of AcGlySCH$_2$PPh$_2$(51) and Non-Glycyl α-Azido Aads

| α-azido acid | peptide | yield (%)$^b$ |
|---|---|---|
| 48-L | AcGly(L)PheNHBn 52-L | 90 |
| 49-L | AcGly(L)Asp(OMe)NHBn 53-L | 91 |
| 48-D | AcGly(D)PheNHBn 52-D | 93 |

TABLE 1-continued

Staudinger Ligation of AcGlySCH$_2$PPh$_2$(51) and Non-Glycyl α-Azido Aads

| α-azido acid | peptide | yield (%)[b] |
|---|---|---|
| 49-D | AcGly(D)Asp(OMe)NHBn 53-D | 95 |
| 50-L | AcGly(L)Ser(Bn)NHBn 54-L | 92 |
| 50-D | AcGly(D)Ser(Bn)NHBn 54-D | 99 |

[a]Reaction conditions: THF/H$_2$O (3:1) at room temperature for 12 h.
[b]Isolated yield product after purification by flash chromatography.

REFERENCES (1) For recent reviews of peptide ligation methodology, see: (a) Tam, J. P.; Yu, Q.; Miao, Z. *Biopolymers* 1999, 51, 311-332. (b) Dawson, P. E.; Kent, S. B. H. *Annu. Rev. Biochem.* 2000, 69, 923-960. (c) Borgia, J. A.; Fields, G. B. *Trends Biotechnol.* 2000, 15, 243-251. (d) Miranda, L. P.; Alewood, P. F. *Biopolymers* 2000, 55, 217-226, (e) Tam, J. P.; Xu, J.; Eom, K. D. *Biopolymers* 2001, 60, 194-205.

(2) Wieland, T.; Bokelmann, E.; Bauer, L.; Lang, H. U.; Lau, H. *Liebigs Ann. Chem.* 1953, 583, 129-149. (b) Dawson, P. E.; Muir, T. W.; Clark-Lewis, I.; Kent, S. B. H. *Science* 1994, 266, 776-779.

(3) Cysteine is uncommon, comprising only 1.7% of the residues in proteins (McCaldon, P.; Argos, P. *Proteins* 1988, 4, 99-122). Modern peptide synthesis is typically limited to peptides of ≦50 residues (ref 1). Hence, most proteins cannot be prepared by any method that allows for the coupling of peptides only at cysteine residues.

(4) (a) Nilsson, B. L.; Kiessling, L. L.; Raines, R. T. *Org. Lett.* 2000, 2, 1939-1941. (b) Nilsson, B. L.; Kiessling, L. L.; Raines, R. T.; *Org. Lett.* 2001, 3, 9-12. For a review, see: (c) Gilbertson, S. *Chemtracts—Org. Chem.* 2001, 14, 524-528.

(5) (a) Staudinger, H.; Meyer, J. *Helv. Chim. Acta* 1919, 2, 635-646. For a review see: (b) Gololobov, Yu. G.; Kasukhi, L. F. *Tetrahedron* 1992, 48, 1353-1406.

(6) For examples in which the acyl donor is attached covalently to the phosphine, see: ref4 and (a) Saxon, E.; Bertozzi, C. R. *Science* 2000, 287, 2007-2010. (b) Saxon, E.; Armstrong, J. I.; Bertozzi, C. R. *Org. Lett.* 2000, 2, 2141-2143. (c) Kiick, K. L.; Saxon, E.; Tirrell, D. A.; Bertozzi, C. R. *Proc. Natl. Acad. Sci. U.S.A.* 2002, 99, 19-24.

(7) For examples in which the acyl donor is not attached to the phosphine, see: (a) Garcia, J.; Urpi, F.; Vilarrasa, J. *Tetrahedron Lett.* 1984, 25, 4841-4844. (b) Garcia, J.; Vilarrasa, J. *Tetrahedron Lett.* 1986, 27, 639-640. (c) Urpi, F.; Vilarrasa, J. *Tetrahedron Lett.* 1986, 27, 4623-4624. (d) Bosch, I.; Romea, P.; Urpi, F.; Vilarrasa, J. *Tetrahedron Lett.* 1993, 34, 4671-4674. (e) Inazu, T.; Kobayashi, K. *Synlett.* 1993, 869-870. (f) Molina, P.; Vilaplana, M.J. *Synthesis-Stuttgart* 1994, 1197-1218. (g) Bosch, I.; Urpi, F.; Vilarrasa, J. *J. Chem. Soc., Chem. Commun.* 1995, 91-92. (h) Shalev, D.E.; Chiacchiera, S.M.; Radkowsky, A.E.; Kosower, E. M. *J. Org. Chem.* 1996, 61,1689-1701. (I) Bosch, I.; Gonzalez, A.; Urpi, F.; Vilarrasa, J. *J. Org. Chem.* 1996, 61, 5638-5643. (j) Maunier, V.; Boullanger, P.; Lafont, D.LJ. *Carbohydr. Chem.* 1997, 16, 23 1-235. (k) Afonso, C.A.M. *Synthetic Commun.* 1998, 28, 261-276. (l) Tang, Z.; Pelletier, J.C. *Tetrahedron Lett.* 1998, 39, 4773-4776. (m) Ariza, X.; Urpi, F.; Viladomat, C.; Vilarrasa, J. *Tetrahedron Lett.* 1998, 39, 9101-9102. (n) Mizuno, M.; Muramoto, I.; Kobayashi, K.; Yaginuma, H.; lnazu, T. *Synthesis-Stuttgart* 1999, 162,165. (o) Mizuno, M.; Haneda, K.; Iguchi, R.; Muramoto, I.; Kawakami, T.; Aimoto, S.; Yamamoto, K.; Inazu, T. *J. Am. Chem. Soc.* 1999, 121, 284-290. (p) Boullanger, P.; Maunier, V.; Lafont, D. *Carbohydr. Res.* 2000, 324, 97-106. (q) Velasco, M.D.; Molina, P.; Fresneda P.M.; Sanz, M.A. *Tetrahedron* 2000, 56, 4079-4084. (r) Malkinson, J.P.; Falconer, R.A.; Toth, I. *J. Org. Chem.* 2000, 65, 5249-5252. (s) Ariza, X.; Pineda, O.; Urpi, F.; Vilarrasa, J. *Tetrahedron Lett.* 2001, 42, 4995-4999.

(8) For information on exploiting the chirality of α-amino acids, see: Coppola, G. M.; Schuster, H. F. *Asymmetric Synthesis.* 1987. John Wiley & Sons, New York.

(9) Lu, W.; Qasim, M. A.; Kent, S. B. H. *J. Am. Chem. Soc.* 1996, 118, 8518-8523.

(10) Zaloom, J.; Roberts, D. C. *J. Org. Chem.* 1981, 46, 5173-5176.

(11) Because the reaction products herein are enantiomers, we actually probe "racemization" (Reist, M.; Testa, B.; Carrupt, P.-A.; Jung, M.; Schurig, V. *Chirality* 1995, 7, 396-400) We use the term "epimerization" to focus attention on the chirality of the α-carbon.

(12) For reviews of borane protection of phosphines see: (a) Brunel, J. M.; Faure, B.; Maffei, M. Coord. *Chem. Rev.* 1998, 180, 665-698. (b) Carboni, B.; Monnier, L. *Tetrahedron* 1999, 55, 1197-1248.

(13) Farrington, G. K.; Kumar, A.; Wedler, F. C. *Org. Prep. Proced. Int.* 1989, 21, 390-392.

(14) Imamoto, T.; Oshiki, T.; Onozawa, T.; Kusumoto, T.; Sato, K. *J. Am. Chem. Soc.* 1990, 112, 5244-5252.

(15) Brisset, H.; Gourdel, Y.; Pellon, P.; Le Corre, M. *Tetrahedron Lett.* 1993, 34, 4523-4526.

(16) Romoff, T. T.; Goodman, M. *J. Peptide Res.* 1997, 49, 281-292.

(17) Lundquist, J. T., IV; Pelletier, J. C. *Org. Lett.* 2001, 3, 781-783.

We claim:
1. A phosphine-borane complex of formula:

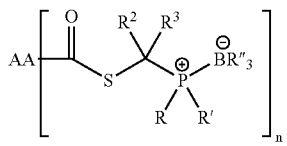

where R and R', independently of one another, are optionally substituted alkyl, aryl or alkoxy groups where R and R' may be the same or different groups and R and R' may be covalently linked to each other;

R", in dependently of other R" in the compound, are selected from H, an optionally substituted alkyl or an optionally substituted aryl group where all three of R" may be the same or each may be different, and any two or three of R" may be covalently linked to each other;

$R^2$ and $R^3$, independently of one another, are selected from H, an optionally substituted alkyl or an optionally substituted aryl group, where $R^2$ and $R^3$ may be covalently linked to each other;

n is a integer; and

AA is an amino acid, peptide or protein or a fully or partially protected derivative thereof.

2. The complex of claim 1 wherein the AA group is an amino acid or a fully or partially protected derivative thereof.

3. The complex of claim 1 wherein the AA group is a peptide or a fully or partially protected derivative thereof.

4. The complex of claim 1 wherein n is 1, 2 or 3.

5. The complex of claim 1 wherein R and R' are optionally substituted alkyl, alkoxy or aryl groups.

6. The complex of claim 1 wherein R and R' are ethyl groups.

7. The complex of claim 1 wherein $R^2$, $R^3$ are H.

8. The complex of claim 1 R" are all H or all small alky groups.

9. A kit for forming an amide bond which comprises one or more phoshine-borane complexes of claim 1.

10. The complex of claim 1 wherein n is 1 and AA is selected from the group consisting of glycine, alanine, valine, leucine, isoleucine, phenylalanine, serine, methionine, proline, tyrosine, tryptophan, lysine, arginine, histidine, asparate, glutamate, asparagine, glutamine, cysteine, methionine, hydroxyproline, γ-carboxyglutamate, O-phosphoserine, ornithine, homoarginine and protected derivatives thereof.

11. The complex of claim 10 wherein n is 1 and AA is a protected derivative of an amino acid selected from the group consisting of glycine, alanine, valine, leucine, isoleucine, phenylalanine, serine, methionine, proline, tyrosine, tryptophan, lysine, arginine, histidine, asparate, glutamate, asparagine, glutamine, cysteine, methionine, hydroxyproline, γ-carboxyglutamate, O-phosphoserine, ornithine, and homoarginine.

12. The complex of claim 1 wherein n is 1 and AA is a protected amino acid.

13. The complex of claim 12 wherein the AA is an N-acetyl protected amino acid.

14. The complex of claim 12 wherein the AA is N-acetyl glycine or N-acetyl phenylalanine.

15. The complex of claim 13 wherein R and R' are phenyl groups.

16. The complex of claim 13 wherein R and R' are alkyl groups.

17. The complex of claim 13 wherein $R^2$ and $R^3$ are H.

18. The complex of claim 16 wherein R and R' are phenyl groups.

19. The complex of claim 17 wherein all R" are H.

20. The complex of claim 1 wherein the AA is a side-group protected amino acid.

21. The complex of claim 20 wherein the AA is a protected aspartate, glutamate, asparagine, or glutamine.

22. The complex of claim 1 wherein the AA is an amino acid having a side-group carrying a carboxyl group and wherein the thioester is formed at the carboxyl group of the amino acid side group.

23. The complex of claim 22 wherein the AA is aspartate or glutamate.

24. The complex of claim 23 which is

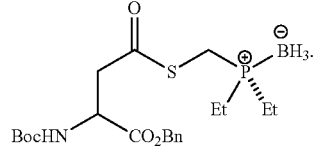

25. A kit for forming an amide bond which comprises one or more phoshine-borane complexes of claim 2.

26. The kit of claim 25 wherein in the phosphine-borane complexes n is 1 and AA is selected from the group consisting of glycine, alanine, valine, leucine, isoleucine, phenylalanine, serine, methionine, proline, tyrosine, tryptophan, lysine, arginine, histidine, asparate, glutamate, asparagine, glutamine, cysteine, methionine, hydroxyproline, γ-carboxyglutamate, O-phosphoserine, ornithine, homoarginine and protected derivatives thereof.

27. The kit of claim 9 further comprising one or more azides.

28. The kit of claim 27 wherein the azide is an azide of an amino acid, a peptide, a protein, a carbohydrate, a monosaccharide, a disaccharide, a trisaccharide, a nucleoside, a reporter, a tag or label.

* * * * *

UNITED STATES PATENT AND TRADEMARK OFFICE
CERTIFICATE OF CORRECTION

| | |
|---|---|
| PATENT NO. | : 7,317,129 B2 |
| APPLICATION NO. | : 11/229926 |
| DATED | : January 8, 2008 |
| INVENTOR(S) | : Raines et al. |

It is certified that error appears in the above-identified patent and that said Letters Patent is hereby corrected as shown below:

Title Page, Item (56)
    Please add the following references to the References Cited and Other Publications.

US Patent No.: 4,066,684, Issue Date: 01/03/1978, Inventor(s): Dorman et al.
    US Patent No.: 6,570,040, Issue Date: 05/27/2003, Inventor(s): Saxon et al.
    Lemieux et al. (1998), "Chemoselective Ligation Reactions with Proteins, Oligosaccharides and Cells," Trends Biotechnol. 16:506-513.
    Lemieux et al. (Apr. 2003), "A Fluorogenic Dye Activated by the Staudinger Ligation," J. Am. Chem. Soc. 125:4708-4709.
    Lu et al. (1996), "Comparative Total Syntheses of Turkey Ovomucoid Third Domain by Both Stepwise Solid Phase Peptide Synthesis and Native Chemical Ligation," J. Am. Chem. Soc. 118:8518-8623.
    Lundberg et al. (1969), Chemical Abstracts (Columbus, Ohio, USA) No. 71:18411. Abstract of Inorganic Chemistry (1969) 8(6):1336-1340.
    Lundquist et al. (Mar. 2001), "Improved Solid-Phase Peptide Synthesis Method Utilizing α-Azide-Protected Amino Acids," Org. Lett. 3:781-783.
    Malkinson et al. (Aug. 2000), "Synthesis of C-Terminal Glycopeptides from Resin-Bound Glycosyl Azides vie a Modified Staudinger Reaction," J. Org. Chem. 65:5249-5252.
    Marahiel et al. (1997), "Modular Peptide Synthetases Involved in Nonribosomal Peptide Synthesis," Chem. Rev. 97:2651-2673.
    Marcaurelle et al. (1998), "Direct Incorporation of Unprotected Ketone Groups into Peptides During Solid-Phase Synthesis: Application to the One-Step Modification of Peptides with Two Different Biophysical Probes for FRET," Tetrahedron Lett. 39:7279-7282.
    Maunier et al. (1997), "Synthesis and Surface-Active Properties of Amphiphilic 6-Aminocarbonyl Derivatives of D-Glucose," Carbohyr. Res. 299:49-57.
    Maunier et al. (1997), "A One-Pot Synthesis of Glycosyl Amides from Glycosyl Azides Using a Modified Staudinger Reaction," J. Carbohydrate Chemistry 16:231-235.
    McCaldon et al. (1998), "Oligopeptide Biasesin Protein Sequences and Their Use in Predicting Protein Coding Regions in Nucleotide Sequences," Proteins 4:99-122.
    Meldal et al. (1997), "Azido Acids in a Novel Method of Solid-Phase Peptide Synthesis," Tetrahedron Lett. 38:2531-2534.
    Merrifield, R. B. (1984), "Solid Phase Synthesis," Science 232: 341-347.

UNITED STATES PATENT AND TRADEMARK OFFICE
CERTIFICATE OF CORRECTION

| | | |
|---|---|---|
| PATENT NO. | : 7,317,129 B2 | |
| APPLICATION NO. | : 11/229926 | |
| DATED | : January 8, 2008 | |
| INVENTOR(S) | : Raines et al. | |

It is certified that error appears in the above-identified patent and that said Letters Patent is hereby corrected as shown below:

1. (Continued)

Miranda et al. (pub. on-line Nov. 2000), "Challenges for Protein Chemical Synthesis in the 21st Century: Bridging Genomics and Proteomics," Biopolymers 55:217-226.
     Mizuno et al. (Jan. 1999), "A Simple Method for the Synthesis of Nβ-Glycosylated-Asparagine and -Glutamine Derivatives," Synthesis-Stuttgart, pp. 162-165.
     Mizuno et al. (Jan. 1999), "Synthesis of a Glycopeptide Containing Oligosaccharides: Chemoenzymatic Synthesis of Eel Calcitonin Analogues Having Natural N-Linked Ooigosaccharides," J. Am. Chem. Soc. 121:284-290.
     Mizuno et al. (2002), Phosphorus, Sulphur, and Silicon, "The New Amide Bond Formation Using Trialkylphosphine," 177:1945.
     Molina et al. (1994), "Iminophosphoranes: Useful Building Blocks for the Preparation of Nitrogen-Containing Heterocycles," Synthesis-Stuttgart, pp. 1197-1218.
     Muir et al. (1997), "Protein Synthesis by Chemical Ligation of Unprotected Peptides in Aqueous Solution," Methods Enzymol. 289: 266-298.
     Muir et al. (1998), "Expressed Protein Ligation: A General Method for Protein Engineering," Proc. Natl. Acad. Sci. U.S.A. 9:6705-6710.
     Nilsson et al. (2000), "Staudinger Ligation: A Peptide from a Thioester and Azide," Org. Lett. 2:1939-1941.
     Nilsson et al. (pub. on-line Dec. 2000), "High-Yielding Staudinger Ligation of a Phosphinothioester and Azide to Form a Peptide," Org. Lett. 3:9-12.
     Nilsson et al. (May 2003), "Protein Assembly by Orthogonal Chemical Ligation Methods," J. Am. Chem. Soc. 125:5468-5269.
     Offer et al. (Jan. 2000), "Nα-2-Mercaptobenzylamine-Assisted Chemical Ligation," Org. Lett. 2:23-26.
     Ohff et al. (1998), "Borane Complexes of Trivalent Organophosphorus Compounds. Versatile Precursors for the Synthesis of Chiral Phosphine Ligands for Asymmetric Catalysis".
     Patel et al. (1995), Chemical Abstracts (Columbus, Ohio, USA) No. 122:133805. Abstract of J. Med. Chem. (1995) 38 (3):435-442.
     Perez-Lourido et al. (Jan. 2000), "Diorganotin (IV) Derivatives of Arenephosphinothiol Ligands. The Crystal Structure of [Ph2Sn{2-(Ph2P)C6H4S}2] and [Me2Sn{2-(Ph2PO)-6-(Me3Si)C6H3S}2],1" J. Organomet. Chem. 595:59-65.
     Perich et al. RB (1988), "Di-tert-butyl N,N-Diethylphosphoramidite. A New Phosphitylating Agent for the Efficient Phosphorylation of Alcohols," Synthesis-Stuttgart 2:142-144.
     Raines, R. T. (1997), "Nature's Transitory Covalent Bond," Nature Struct. Biol. 4: 424-427.

UNITED STATES PATENT AND TRADEMARK OFFICE
CERTIFICATE OF CORRECTION

PATENT NO.          : 7,317,129 B2
APPLICATION NO. : 11/229926
DATED                   : January 8, 2008
INVENTOR(S)        : Raines et al.

It is certified that error appears in the above-identified patent and that said Letters Patent is hereby corrected as shown below:

1. (Continued)
Ravindar et al. (1992), "A Novel Convenient Synthesis of Aryl Phosphines Containing Reactive Functional Groups," Synth. Comm. 22:1453-1459.
    Reist et al. (1995), "Racemization, Enantiomerization, Diastereomerization, and Epimerization - Their Meaning and Pharmacological Significance," Chirality 7:396-400 (Abstract only).
    Romoff et al. (1997), "Urethane-Protected N-Carboxyanhydrides (UNCAs) as Unique Reactants for the Study of Intrinsic Racemization Tendencies in Peptide Synthesis," J. Peptide Res. 49:281-292.
    Saxon et al. (Mar. 2000), "Cell Surface Engineering by a Modified Staudinger Reaction," Science 287:2007-2010.
    Saxon et al. (Aug. 1999), "Development of a New Chemoselective Ligation Reaction," Abstracts of Papers American Chemical Society 218:(1-2), pp. Carb 23.
    Saxon et al. (June 2000), "A "Traceless" Staudinger Ligation for the Chemoselective Synthesis of Amide Bonds," Org. Lett. 2:2141-2143.
    Saxon et al. (Dec. 2002), "Investigating Cellular Metabolism of Synthetic Azidosugars with the Staudinger Ligation," J. Am. Chem. Soc. 124:14893-14902.
    Schneider et al. (1965), "Studies on the Direct Neutral Penicilloylation of Functional Groups Occurring on Proteins," Biochim. Biophys. Acta 168:27-35.
    Shalev et al. (1996), "Sequence of Reactant Combination Alters the Course of the Staudinger Reaction of Azides with Acyl Derivatives. Dimanes. 30." J. Org. Chem. 61:1689-1701.
    Shin et al. (Dec. 1999), "Fmoc-Based Synthesis of Peptide-α Thioesters: Application to the Total Chemical Synthesis of a Glycoprotein by Native Chemical Ligation," J. Am. Chem. Soc. 121:11684-11689.
    Soellner et al. (pub. on-line June 2002), "Staudinger ligation of alpha-azido acids retains stereochemistry," J. Org. Chem. 67:4993-4996.
    Soellner et al. (Oct. 2003) "Site-Specific Protein Immobilization by Staudinger Ligation," J. Am. Chem. Soc. 125:11790-11791.
    Staudinger et al. (1919), "Uber neue organische Phosphorverbindunger III. Phosphinmethylenderivate und Phosphinimine," (In German) J. Helv. Chim. Acta 2:635-646.
    Sugama et al. (Jul. 2001), "P-Chirogenic Phosphine/Sulfide Hybrid Ligands," Synthesis, (2001) 2348-2353.
    Swinnen et al. (Jul. 2000), "Facile, Fmoc-Compatible Solid-Phase Synthesis of Peptide C-Terminal Thioesters," Org. Lett. 2:2439-2442.
    Tam et al. (pub. on-line Feb. 2000), "Orthogonal Ligation Strategies for Peptide and Protein," Biopolymers 51:311-332.
    Tam et al. (pub. on-line Dec. 2001), "Methods and Strategies of Peptide Ligation," Biopolymers 60:194-204.

UNITED STATES PATENT AND TRADEMARK OFFICE
CERTIFICATE OF CORRECTION

| | |
|---|---|
| PATENT NO. | : 7,317,129 B2 |
| APPLICATION NO. | : 11/229926 |
| DATED | : January 8, 2008 |
| INVENTOR(S) | : Raines et al. |

It is certified that error appears in the above-identified patent and that said Letters Patent is hereby corrected as shown below:

1. (Continued)

Tam et al. (pub. on-line Dec. 2001), "Methods and Strategies of Peptide Ligation," Biopolymers 60:194-204.
    Tam et al. (1995), "Peptide Synthesis Using Unprotected Peptides Through Orthogonal Coupling Methods," Proc. Natl. Acad. Sci. U.S.A. 92:12485-12489.
    Tam, J.P. (1988), "Synthetic Peptide Vaccine Design: Synthesis and Properties of a High-Density Multiple Antigenic Peptide System," Proc. Natl. Acad. Sci. U.S.A. 85:5409-5413.
    Tang et al. (1998), "Preparation of Amides from Acids and Resin Bound Azides: Suppression of Intramolecular Lactam Formation," Tetrahedron Lett. 39:4773-4776.
    Urpi et al. (1986), "New Synthetic 'Tricks'. Advantages of Using Triethylphosphine in Some Phosphorus-Based Reactions," Tetrahedron Lett 27:4623-4624.
    Vedejs et al. (1993), "Tributylphosphine: A Remarkable Acylation Catalyst," J. Am. Chem. Soc. 115: 3358-3359.
    Velasco et al. (Jun. 2000), "Isolation, Reactivity and Intramolecular Trapping of Phosphazide Intermediates in the Staudinger Reaction of Tertiary Phosphines with Azides," Tetrahedron 56:4079-4084.
    von Dohren et al. (1997), "Multifunctional Peptide Synthetases," Chem. Rev. 97:2675-2705.
    Wieland et al. (1953), "Uber Peptidsyntehsen. 8. Mitteilung," (In German) Liebigs Ann. Chem. 583:129-149.
    Wilken et al. (1998), "Chemical protein synthesis," Curr. Opin. Biotechnol. 9:412-426.
    Wilt et al. (1985), "A New synthesis of Peptides from Azides and Unactivated Carboxylic Acids," J. Org. Chem. 50:2601-2603.
    Woycechowsky et al. (Dec. 1999), "A Small-Molecule Catalyst of Protein Folding in Vitro and in Vivo," Chem.Biol. 6:871-879.
    Zaloom et al. (1981), "Preparation of Azido Derivatives from Amino Acids and Peptides by Diazo Transfer," J. Org. Chem. 46:5173-5176.

UNITED STATES PATENT AND TRADEMARK OFFICE
CERTIFICATE OF CORRECTION

PATENT NO. : 7,317,129 B2
APPLICATION NO. : 11/229926
DATED : January 8, 2008
INVENTOR(S) : Raines et al.

It is certified that error appears in the above-identified patent and that said Letters Patent is hereby corrected as shown below:

Column 4, Scheme 2, near Formula 12, replace "coomplex" with --complex--
Column 6, Line 10, replace "R2 and R3" with --$R^2$ and $R^3$--
Column 6, Line 19, replace "carboxy" with --carboxyl--
Column 7, Scheme 3b, Formula 1b, replace "HS" with --SH--
Column 8, Scheme 4A-continued, near Formula 30, replace "IVA" with --IVB--
Column 8, Scheme 4A-continued, near Formula 30, replace "31" with --32--
Column 8, Scheme 4B, near Formula 30b, replace "3. KOH" with --2. KOH--
Column 9, Line 6, replace "additional" with --additionally--
Column 11, Line 17, replace "or" with --of--
Column 11, Line 19, replace "selected" with --select--
Column 11, Line 21, replace "R5" with --$R^5$--
Column 14, Line 63, replace "1b" with --11b--
Column 15, Line 17, replace "6-" with --δ- --
Column 19, Line 15, replace "C." with --C--
Column 22, Line 20, replace "(I)" with --(i)--
Column 22, Line 24, replace "(I)" with --(l)--

Please correct the following in the Claims of the issued patent:

1. Claim 1, Line 14, replace "in dependently" with --independently--
2. Claim 7, Line 37, replace "R2, R3," with --$R^2$, and $R^3$--
3. Claim 8, Line 38, replace "Claim 1" with --Claim 1 wherein--

Signed and Sealed this

Twenty-eighth Day of October, 2008

JON W. DUDAS
*Director of the United States Patent and Trademark Office*

UNITED STATES PATENT AND TRADEMARK OFFICE
CERTIFICATE OF CORRECTION

PATENT NO. : 7,317,129 B2
APPLICATION NO. : 11/229926
DATED : January 8, 2008
INVENTOR(S) : Raines et al.

It is certified that error appears in the above-identified patent and that said Letters Patent is hereby corrected as shown below:

Title Page, Item (56)
Please add the following references to the References Cited and Other Publications.

US Patent No.: 4,066,684, Issue Date: 01/03/1978, Inventor(s): Dorman et al.
US Patent No.: 6,570,040, Issue Date: 05/27/2003, Inventor(s): Saxon et al.
Lemieux et al. (1998), "Chemoselective Ligation Reactions with Proteins, Oligosaccharides and Cells," Trends Biotechnol. 16:506-513.
Lemieux et al. (Apr. 2003), "A Fluorogenic Dye Activated by the Staudinger Ligation," J. Am. Chem. Soc. 125:4708-4709.
Lu et al. (1996), "Comparative Total Syntheses of Turkey Ovomucoid Third Domain by Both Stepwise Solid Phase Peptide Synthesis and Native Chemical Ligation," J. Am. Chem. Soc. 118:8518-8623.
Lundberg et al. (1969), Chemical Abstracts (Columbus, Ohio, USA) No. 71:18411. Abstract of Inorganic Chemistry (1969) 8(6):1336-1340.
Lundquist et al. (Mar. 2001), "Improved Solid-Phase Peptide Synthesis Method Utilizing α-Azide-Protected Amino Acids," Org. Lett. 3:781-783.
Malkinson et al. (Aug. 2000), "Synthesis of C-Terminal Glycopeptides from Resin-Bound Glycosyl Azides vie a Modified Staudinger Reaction," J. Org. Chem. 65:5249-5252.
Marahiel et al. (1997), "Modular Peptide Synthetases Involved in Nonribosomal Peptide Synthesis," Chem. Rev. 97:2651-2673.
Marcaurelle et al. (1998), "Direct Incorporation of Unprotected Ketone Groups into Peptides During Solid-Phase Synthesis: Application to the One-Step Modification of Peptides with Two Different Biophysical Probes for FRET," Tetrahedron Lett. 39:7279-7282.
Maunier et al. (1997), "Synthesis and Surface-Active Properties of Amphiphilic 6-Aminocarbonyl Derivatives of D-Glucose," Carbohyr. Res. 299:49-57.
Maunier et al. (1997), "A One-Pot Synthesis of Glycosyl Amides from Glycosyl Azides Using a Modified Staudinger Reaction," J. Carbohydrate Chemistry 16:231-235.
McCaldon et al. (1998), "Oligopeptide Biasesin Protein Sequences and Their Use in Predicting Protein Coding Regions in Nucleotide Sequences," Proteins 4:99-122.
Meldal et al. (1997), "Azido Acids in a Novel Method of Solid-Phase Peptide Synthesis," Tetrahedron Lett. 38:2531-2534.
Merrifield, R. B. (1984), "Solid Phase Synthesis," Science 232: 341-347.

UNITED STATES PATENT AND TRADEMARK OFFICE
CERTIFICATE OF CORRECTION

PATENT NO.        : 7,317,129 B2
APPLICATION NO. : 11/229926
DATED             : January 8, 2008
INVENTOR(S)       : Raines et al.

It is certified that error appears in the above-identified patent and that said Letters Patent is hereby corrected as shown below:

1. (Continued)

Miranda et al. (pub. on-line Nov. 2000), "Challenges for Protein Chemical Synthesis in the 21st Century: Bridging Genomics and Proteomics," Biopolymers 55:217-226.
     Mizuno et al. (Jan. 1999), "A Simple Method for the Synthesis of Nβ-Glycosylated-Asparagine and -Glutamine Derivatives," Synthesis-Stuttgart, pp. 162-165.
     Mizuno et al. (Jan. 1999), "Synthesis of a Glycopeptide Containing Oligosaccharides: Chemoenzymatic Synthesis of Eel Calcitonin Analogues Having Natural N-Linked Ooigosaccharides," J. Am. Chem. Soc. 121:284-290.
     Mizuno et al. (2002), Phosphorus, Sulphur, and Silicon, "The New Amide Bond Formation Using Trialkylphosphine," 177:1945.
     Molina et al. (1994), "Iminophosphoranes: Useful Building Blocks for the Preparation of Nitrogen-Containing Heterocycles," Synthesis-Stuttgart, pp. 1197-1218.
     Muir et al. (1997), "Protein Synthesis by Chemical Ligation of Unprotected Peptides in Aqueous Solution," Methods Enzymol. 289: 266-298.
     Muir et al. (1998), "Expressed Protein Ligation: A General Method for Protein Engineering," Proc. Natl. Acad. Sci. U.S.A. 9:6705-6710.
     Nilsson et al. (2000), "Staudinger Ligation: A Peptide from a Thioester and Azide," Org. Lett. 2:1939-1941.
     Nilsson et al. (pub. on-line Dec. 2000), "High-Yielding Staudinger Ligation of a Phosphinothioester and Azide to Form a Peptide," Org. Lett. 3:9-12.
     Nilsson et al. (May 2003), "Protein Assembly by Orthogonal Chemical Ligation Methods," J. Am. Chem. Soc. 125:5468-5269.
     Offer et al. (Jan. 2000), "Nα-2-Mercaptobenzylamine-Assisted Chemical Ligation," Org. Lett. 2:23-26.
     Ohff et al. (1998), "Borane Complexes of Trivalent Organophosphorus Compounds. Versatile Precursors for the Synthesis of Chiral Phosphine Ligands for Asymmetric Catalysis".
     Patel et al. (1995), Chemical Abstracts (Columbus, Ohio, USA) No. 122:133805. Abstract of J. Med. Chem. (1995) 38 (3):435-442.
     Perez-Lourido et al. (Jan. 2000), "Diorganotin (IV) Derivatives of Arenephosphinothiol Ligands. The Crystal Structure of [Ph2Sn{2-(Ph2P)C6H4S}2] and [Me2Sn{2-(Ph2PO)-6-(Me3Si)C6H3S}2],1" J. Organomet. Chem. 595:59-65.
     Perich et al. RB (1988), "Di-tert-butyl N,N-Diethylphosphoramidite. A New Phosphitylating Agent for the Efficient Phosphorylation of Alcohols," Synthesis-Stuttgart 2:142-144.
     Raines, R. T. (1997), "Nature's Transitory Covalent Bond," Nature Struct. Biol. 4: 424-427.

UNITED STATES PATENT AND TRADEMARK OFFICE
CERTIFICATE OF CORRECTION

PATENT NO. : 7,317,129 B2
APPLICATION NO. : 11/229926
DATED : January 8, 2008
INVENTOR(S) : Raines et al.

It is certified that error appears in the above-identified patent and that said Letters Patent is hereby corrected as shown below:

1. (Continued)
Ravindar et al. (1992), "A Novel Convenient Synthesis of Aryl Phosphines Containing Reactive Functional Groups," Synth. Comm. 22:1453-1459.

Reist et al. (1995), "Racemization, Enantiomerization, Diastereomerization, and Epimerization - Their Meaning and Pharmacological Significance," Chirality 7:396-400 (Abstract only).

Romoff et al. (1997), "Urethane-Protected N-Carboxyanhydrides (UNCAs) as Unique Reactants for the Study of Intrinsic Racemization Tendencies in Peptide Synthesis," J. Peptide Res. 49:281-292.

Saxon et al. (Mar. 2000), "Cell Surface Engineering by a Modified Staudinger Reaction," Science 287:2007-2010.

Saxon et al. (Aug. 1999), "Development of a New Chemoselective Ligation Reaction," Abstracts of Papers American Chemical Society 218:(1-2), pp. Carb 23.

Saxon et al. (June 2000), "A "Traceless" Staudinger Ligation for the Chemoselective Synthesis of Amide Bonds," Org. Lett. 2:2141-2143.

Saxon et al. (Dec. 2002), "Investigating Cellular Metabolism of Synthetic Azidosugars with the Staudinger Ligation," J. Am. Chem. Soc. 124:14893-14902.

Schneider et al. (1965), "Studies on the Direct Neutral Penicilloylation of Functional Groups Occurring on Proteins," Biochim. Biophys. Acta 168:27-35.

Shalev et al. (1996), "Sequence of Reactant Combination Alters the Course of the Staudinger Reaction of Azides with Acyl Derivatives. Dimanes. 30." J. Org. Chem. 61:1689-1701.

Shin et al. (Dec. 1999), "Fmoc-Based Synthesis of Peptide-α Thioesters: Application to the Total Chemical Synthesis of a Glycoprotein by Native Chemical Ligation," J. Am. Chem. Soc. 121:11684-11689.

Soellner et al. (pub. on-line June 2002), "Staudinger ligation of alpha-azido acids retains stereochemistry," J. Org. Chem. 67:4993-4996.

Soellner et al. (Oct. 2003) "Site-Specific Protein Immobilization by Staudinger Ligation," J. Am. Chem. Soc. 125:11790-11791.

Staudinger et al. (1919), "Uber neue organische Phosphorverbindunger III. Phosphinmethylenderivate und Phosphinimine," (In German) J. Helv. Chim. Acta 2:635-646.

Sugama et al. (Jul. 2001), "P-Chirogenic Phosphine/Sulfide Hybrid Ligands," Synthesis, (2001) 2348-2353.

Swinnen et al. (Jul. 2000), "Facile, Fmoc-Compatible Solid-Phase Synthesis of Peptide C-Terminal Thioesters," Org. Lett. 2:2439-2442.

Tam et al. (pub. on-line Feb. 2000), "Orthogonal Ligation Strategies for Peptide and Protein," Biopolymers 51:311-332.

Tam et al. (pub. on-line Dec. 2001), "Methods and Strategies of Peptide Ligation," Biopolymers 60:194-204.

UNITED STATES PATENT AND TRADEMARK OFFICE
CERTIFICATE OF CORRECTION

| | |
|---|---|
| PATENT NO. | : 7,317,129 B2 |
| APPLICATION NO. | : 11/229926 |
| DATED | : January 8, 2008 |
| INVENTOR(S) | : Raines et al. |

It is certified that error appears in the above-identified patent and that said Letters Patent is hereby corrected as shown below:

1. (Continued)

Tam et al. (pub. on-line Dec. 2001), "Methods and Strategies of Peptide Ligation," Biopolymers 60:194-204.

Tam et al. (1995), "Peptide Synthesis Using Unprotected Peptides Through Orthogonal Coupling Methods," Proc. Natl. Acad. Sci. U.S.A. 92:12485-12489.

Tam, J.P. (1988), "Synthetic Peptide Vaccine Design: Synthesis and Properties of a High-Density Multiple Antigenic Peptide System," Proc. Natl. Acad. Sci. U.S.A. 85:5409-5413.

Tang et al. (1998), "Preparation of Amides from Acids and Resin Bound Azides: Suppression of Intramolecular Lactam Formation," Tetrahedron Lett. 39:4773-4776.

Urpi et al. (1986), "New Synthetic 'Tricks'. Advantages of Using Triethylphosphine in Some Phosphorus-Based Reactions," Tetrahedron Lett 27:4623-4624.

Vedejs et al. (1993), "Tributylphosphine: A Remarkable Acylation Catalyst," J. Am. Chem. Soc. 115: 3358-3359.

Velasco et al. (Jun. 2000), "Isolation, Reactivity and Intramolecular Trapping of Phosphazide Intermediates in the Staudinger Reaction of Tertiary Phosphines with Azides," Tetrahedron 56:4079-4084.

von Dohren et al. (1997), "Multifunctional Peptide Synthetases," Chem. Rev. 97:2675-2705.

Wieland et al. (1953), "Uber Peptidsyntehsen. 8. Mitteilung," (In German) Liebigs Ann. Chem. 583:129-149.

Wilken et al. (1998), "Chemical protein synthesis," Curr. Opin. Biotechnol. 9:412-426.

Wilt et al. (1985), "A New synthesis of Peptides from Azides and Unactivated Carboxylic Acids," J. Org. Chem. 50:2601-2603.

Woycechowsky et al. (Dec. 1999), "A Small-Molecule Catalyst of Protein Folding in Vitro and in Vivo," Chem.Biol. 6:871-879.

Zaloom et al. (1981), "Preparation of Azido Derivatives from Amino Acids and Peptides by Diazo Transfer," J. Org. Chem. 46:5173-5176.

UNITED STATES PATENT AND TRADEMARK OFFICE
CERTIFICATE OF CORRECTION

PATENT NO. : 7,317,129 B2
APPLICATION NO. : 11/229926
DATED : January 8, 2008
INVENTOR(S) : Raines et al.

It is certified that error appears in the above-identified patent and that said Letters Patent is hereby corrected as shown below:

Column 4, Scheme 2, near Formula 12, replace "coomplex" with --complex--
Column 6, Line 10, replace "R2 and R3" with --$R^2$ and $R^3$--
Column 6, Line 19, replace "carboxy" with --carboxyl--
Column 7, Scheme 3b, Formula 1b, replace "HS" with --SH--
Column 8, Scheme 4A-continued, near Formula 30, replace "IVA" with --IVB--
Column 8, Scheme 4A-continued, near Formula 30, replace "31" with --32--
Column 8, Scheme 4B, near Formula 30b, replace "3. KOH" with --2. KOH--
Column 9, Line 6, replace "additional" with --additionally--
Column 11, Line 17, replace "or" with --of--
Column 11, Line 19, replace "selected" with --select--
Column 11, Line 21, replace "R5" with --$R^5$--
Column 14, Line 63, replace "1b" with --11b--
Column 15, Line 17, replace "6-" with --δ- --
Column 19, Line 15, replace "C." with --C--
Column 22, Line 20, replace "(I)" with --(i)--
Column 22, Line 24, replace "(I)" with --(l)--

Please correct the following in the Claims of the issued patent:

<u>Column 23</u>
1. Claim 1, Line 14, replace "in dependently" with --independently--
2. Claim 7, Line 37, replace "R2, R3," with --$R^2$, and $R^3$--
3. Claim 8, Line 38, replace "Claim 1" with --Claim 1 wherein--

This certificate supersedes the Certificate of Correction issued October 28, 2008.

Signed and Sealed this

Eighteenth Day of November, 2008

JON W. DUDAS
*Director of the United States Patent and Trademark Office*